US010570401B2

(12) United States Patent
Rickard et al.

(10) Patent No.: US 10,570,401 B2
(45) Date of Patent: Feb. 25, 2020

(54) COMPOSITIONS AND METHOD FOR DESTABILIZING, ALTERING, AND DISPERSING BIOFILMS

(71) Applicants: THE REGENTS OF THE UNIVERSITY OF MICHIGAN, Ann Arbor, MI (US); COLGATE-PALMOLIVE COMPANY, New York, NY (US)

(72) Inventors: Alexander Rickard, Ann Arbor, MI (US); Adam Underwood, Cheektowaga, NY (US); Laurence Du-Thumm, Princeton, NJ (US)

(73) Assignees: THE REGENTS OF THE UNIVERSITY OF MICHIGAN, Ann Arbor, MI (US); COLGATE-PALMOLIVE COMPANY, New York, NY (US)

(*) Notice: Subject to any disclaimer, the term of this patent is extended or adjusted under 35 U.S.C. 154(b) by 104 days.

(21) Appl. No.: 15/134,007

(22) Filed: Apr. 20, 2016

(65) Prior Publication Data
US 2016/0304886 A1 Oct. 20, 2016

Related U.S. Application Data

(63) Continuation of application No. 15/023,111, filed as application No. PCT/US2014/057235 on Sep. 24, 2014, now abandoned.

(60) Provisional application No. 61/972,920, filed on Mar. 31, 2014, provisional application No. 61/881,762, filed on Sep. 24, 2013.

(51) Int. Cl.
C12N 15/74 (2006.01)
G01N 33/68 (2006.01)
A61K 31/198 (2006.01)
A61K 31/4425 (2006.01)
A61K 9/00 (2006.01)
A61Q 11/00 (2006.01)
G01N 33/84 (2006.01)

(52) U.S. Cl.
CPC .......... *C12N 15/746* (2013.01); *A61K 9/0053* (2013.01); *A61K 31/198* (2013.01); *A61K 31/4425* (2013.01); *G01N 33/6812* (2013.01); *G01N 33/84* (2013.01); *G01N 2500/10* (2013.01)

(58) Field of Classification Search
CPC .............. A61K 2300/00; A61K 31/198; A61K 31/4425; A61K 9/0053; A61K 8/44; A61K 8/4926; A61Q 11/00; C12N 15/746; C12Q 1/14; G01N 2500/10; G01N 33/6812; G01N 33/84
See application file for complete search history.

(56) References Cited

U.S. PATENT DOCUMENTS

| 2003/0170184 A1 | 9/2003 | Comelli et al. |
| 2005/0207995 A1 | 9/2005 | Gregory et al. |
| 2011/0318282 A1 | 12/2011 | Ratcliff et al. |
| 2012/0141588 A1 | 6/2012 | Chopra |
| 2013/0224270 A1 | 8/2013 | Robinson et al. |
| 2016/0235698 A1 | 8/2016 | Rickard et al. |
| 2016/0304886 A1 | 10/2016 | Rickard et al. |

FOREIGN PATENT DOCUMENTS

| WO | 2011/162756 A1 | 12/2011 |
| WO | 2013/063695 A1 | 5/2013 |
| WO | 2013/089735 A1 | 6/2013 |
| WO | 2015/048146 A1 | 4/2015 |

OTHER PUBLICATIONS

Rickard et al., "Shear rate moderates community diversity in freshwater biofilms." Appl Environ Microbiol. Dec. 2004;70(12):7426-35.
Rogers et al., "The utilization of casein and amino acids by *Streptococcus sanguis* P4A7 in continuous culture" J Gen Microbiol. Dec. 1990;136(12):2545-50.
Sato et al., "Coaggregation between Prevotella oris and Porphyromonas gingivalis" Journal of Microbiology, Immunology and Infection (2014) 47, 182-186.
Sauer et al., "Characterization of nutrient-induced dispersion in Pseudomonas aeruginosa PAO1 biofilm." J Bacteriol. Nov. 2004;186(21):7312-26.
Sauer et al., "Pseudomonas aeruginosa displays multiple phenotypes during development as a biofilm." J Bacteriol. Feb. 2002;184(4):1140-54.
Simoes et al., "Intergeneric coaggregation among drinking water bacteria: evidence of a role for Acinetobacter calcoaceticus as a bridging bacterium." Appl Environ Microbiol. Feb. 2008;74(4):1259-63.
Spoering et al., "Quorum sensing and DNA release in bacterial biofilms." Curr Opin Microbiol. Apr. 2006;9(2):133-7.
Stewart et al., "Antibiotic resistance of bacteria in biofilms." Lancet. Jul. 14, 2001;358(9276)135-8.
Stoodley et al., "Biofilms as complex differentiated communities." Annu Rev Microbiol. 2002;56:187-209.
Takemoto et al., "Purification of arginine-sensitive hemagglutinin from Fusobacterium nucleatum and its role in coaggregation." J Periodontal Res. Jan. 2003;28(1):21-6.
Terleckyi et al., "Amino acid requirements of *Streptococcus mutans* and other oral streptococci." Infect Immun. Apr. 1975;11(4):656-64.

(Continued)

*Primary Examiner* — Sarvamangala Devi
(74) *Attorney, Agent, or Firm* — Casimir Jones, S.C.; Tanya Arenson

(57) ABSTRACT

The present disclosure relates to compositions and methods for destabilizing biofilms, altering biofilm 3D structure, and dispersing biofilms, in order to enhance biofilm cell removal and/or sensitivity to other agents (e.g., environmental or co-applied treatments). In particular, the present disclosure relates to the use of L-arginine in the removal and/or sensitization (e.g., to antimicrobials) of microorganisms in medical, industrial, domestic, or environmental applications, as well as treatment of bacterial infections (e.g., in biofilms).

8 Claims, 12 Drawing Sheets

(56) References Cited

OTHER PUBLICATIONS

Van Houdt et al., "Role of bacterial cell surface structures in *Escherichia coli* biofilm formation." Res Microbiol. Jun.-Jul. 2005;156(5-6):626-33.
Van Wuyckhuyse et al., "Association of free arginine and lysine concentrations in human parotid saliva with caries experience." J Dent Res. Feb. 1995;74(2):686-90.
Whitchurch et al., "Extracellular DNA required for bacterial biofilm formation." Science. Feb. 22, 2002;295(5559):1487.
Whitmore et al., "The pathogenic persona of community-associated oral streptococci." Mol Microbiol. Jul. 2011;81(2):305-14.
Wolfaardt et al., "In situ Characterization of Biofilm Exopolymers Involved in the Accumulation of Chlorinated Organics" Microb Ecol. May 1998;35(3):213-23.
Xavier et al., "Biofilm-control strategies based on enzymic disruption of the extracellular polymeric substance matrix—a modelling study." Microbiology. Dec. 2005;151(Pt 12):3817-32.
Xu et al., "A systems-level approach for investigating Pseudomonas aeruginosa biofilm formation." PLoS One. 2013;8(2):e57050.
Zeng et al., "Characterization of cis-acting sites controlling arginine deiminase gene expression in *Streptococcus gordonii*." J Bacteriol. Feb. 2006;188(3):941-9.
Zhu et al., "The role of hydrogen peroxide in environmental adaptation of oral microbial communities." Oxid Med Cell Longev. 2012;2012:717843.
Cowman et al., "Amino acid requirements and proteolytic activity of *Streptococcus sanguis*." Appl Microbiol. Sep. 1975;30(3):374-80.
Cowman et al., "Influence of incubation atmosphere on growth and amino acid requirements of *Streptococcus mutans*." Appl Microbiol. Jan. 1974;27(1):86-92.
Acevedo et al., "Clinical evaluation of the ability of CaviStat in a mint confection to inhibit the development of dental caries in children." J Clin Dent. 2008;19(1):1-8.
Aspiras et al., "Expression of green fluorescent protein in *Streptococcus gordonii* DL1 and its use as a species-specific marker in coadhesion with *Streptococcus oralis* 34 in saliva-conditioned biofilms in vitro." Appl Environ Microbiol. Sep. 2000;66(9):4074-83.
Hendrickson et al., "Proteomics of *Streptococcus gordonii* within a model developing oral microbial community." BMC Microbiol. Sep. 18, 2012;12:211.
Jakubovics et al., "Regulation of gene expression in a mixed-genus community: stabilized arginine biosynthesis in *Streptococcus gordonii* by coaggregation with Actinomyces naeslundii." J Bacteriol. May 2008;190(10):3646-57.
Kamaguchi et al., "Coaggregation of Porphyromonas gingivalis and Prevotella intermedia." Microbiol Immunol. 2001;45(9):649-56.
Kraivaphan et al., "Two-year caries clinical study of the efficacy of novel dentifrices containing 1.5% arginine, an insoluble calcium compound and 1,450 ppm fluoride." Caries Res. 2013;47(6):582-90.
Nance et al., "A high-throughput microfluidic dental plaque biofilm system to visualize and quantify the effect of antimicrobials." J Antimicrob Chemother. Nov. 2013;68(11):2550-60.
Wang et al., "Dental plaque pH recovery effect of arginine bicarbonate rinse in vivo." Chin J Dent Res. 2012;15(2):115-20.
Zhang et al., "Dynamic changes in the initial colonization of Actinomyces naeslundii and *Streptococcus gordonii* using a new animal model." Jpn J Infect Dis. 2013;66(1)11-6.
European Search Report of related Application No. 14847319.2, dated Feb. 15, 2017, 10 pages.
European Search Report of related Application No. 16195796.4, dated Mar. 9, 2017, 7 pages.
Bernier et al., "Modulation of Pseudomonas aeruginosa surface-associated group behaviors by individual amino acids through c-di-GMP signaling." Res Microbiol. Sep. 2011;162(7):680-8.
Borriello et al., "Oxygen limitation contributes to antibiotic tolerance of Pseudomonas aeruginosa in biofilms." Antimicrob Agents Chemother. Jul. 2004;48(7):2659-64.
Bowden et al., "Nutritional influences on biofilm development." Adv Dent Res. Apr. 1997;11(1):81-99.
Buswell et al., "Extended survival and persistence of *Campylobacter* spp. in water and aquatic biofilms and their detection by immunofluorescent-antibody and -rRNA staining." Appl Environ Microbiol. Feb. 1998;64(2):733-41.
Chen et al., "Biofilm removal caused by chemical treatments" Water Research, vol. 34, Issue 17, Dec. 2000, pp. 4229-4233.
Cowman et al., "Amino acid requirements and human saliva as a nitrogen source for *Streptococcus salivarius* and *Streptococcus mitior*." J Dent Res. Jan. 1978;57(1):48.
Cuadra-Saenz et al., "Autoinducer-2 influences interactions amongst pioneer colonizing streptococci in oral biofilms." Microbiology. Jul. 2012;158(Pt 7):1783-95.
Cugini et al., "Arginine deiminase inhibits Porphyromonas gingivalis surface attachment." Microbiology. Feb. 2013;159(Pt 2):275-85.
Davies et al., "A fatty acid messenger is responsible for inducing dispersion in microbial biofilms." J Bacterial. Mar. 2009;191(5):1393-403.
Davis et al., "Microscopic and physiologic evidence for biofilm-associated wound colonization in vivo." Wound Repair Regen. Jan.-Feb. 2008;16(1):23-9.
Edwards et al., "Association of a high-molecular weight arginine-binding protein of Fusobacterium nucleatum ATCC 10953 with adhesion to secretory immunoglobulin A and coaggregation with *Streptococcus cristatus*." Oral Microbiol Immunol. Aug. 2007;22(4):217-24.
Egland et al., "Interspecies communication in *Streptococcus gordonii*—Veillonella atypica biofilms: signaling in flow conditions requires juxtaposition." Proc Natl Acad Sci U S A. Nov. 30, 2004;101(48):16917-22.
Eke et al., "Prevalence of periodontitis in adults in the United States: 2009 and 2010." J Dent Res. Oct. 2012;91(10):914-20.
Ellen et al., "Inhibition of Actinomyces viscosus—Porphyromonas gingivalis coadhesion by trypsin and other proteins." Oral Microbiol Immunol. Aug. 1992;7(4):198-203.
England et al. "Global regulation of gene expression and cell differentiation in Caulobacter crescentus in response to nutrient availability."J Bacteriol. Feb. 2010;192(3):819-33.
Flemming et al., "Relevance of microbial extracellular polymeric substances (EPSs)—Part II: Technical aspects." Water Sci Technol. 2001;43(6)9-16.
George et al., "Coaggregation studies of the *Eubacterium* species." Oral Microbiol Immunol. Oct. 1992;7(5):285-90.
Gibbons et al., "Interbacterial aggregation of plaque bacteria." Arch Oral Biol. Dec. 1970;15(12):1397-400.
Hojo et al., "Bacterial interactions in dental biofilm development." J Dent Res. Nov. 2009;88(11):982-90.
Imamura et al., "Fusarium and Candida albicans biofilms on soft contact lenses: model development, influence of lens type, and susceptibility to lens care solutions." Antimicrob Agents Chemother. Jan. 2008;52(1):171-82.
International Search Report of parent PCT Application No. PCT/US2014/057235, dated Mar. 5, 2015, 18 pages.
Jakubovics et al., "The road to ruin: the formation of disease-associated oral biofilms." Oral Dis. Nov. 2010;16(8):729-39.
Kaplan et al., "Enzymatic detachment of *Staphylococcus epidermidis* biofilms." Antimicrob Agents Chemother. Jul. 2004;48(7):2633-6.
Kaplan et al., "The Fusobacterium nucleatum outer membrane protein RadD is an arginine-inhibitable adhesin required for interspecies adherence and the structured architecture of multispecies biofilm." Mol Microbiol. Jan. 2009;71(1):35-47.
Khemaleelakul et al., "Autoaggregation and coaggregation of bacteria associated with acute endodontic infections." J Endod. Apr. 2006;32(4):312-8.
Kolenbrander et al., "Bacterial interactions and successions during plaque development." Periodontol 2000. 2006;42:47-79.
Kolenbrander et al., "Oral microbial communities: biofilms, interactions, and genetic systems." Annu Rev Microbiol. 2000;54:413-37.
Kolenbrander et al., "Oral multispecies biofilm development and the key role of cell-cell distance." Nat Rev Microbiol. Jul. 2010;8(7):471-80.

(56) References Cited

OTHER PUBLICATIONS

Kuo et al., "Associations between periodontal diseases and systemic diseases: a review of the inter-relationships and interactions with diabetes, respiratory diseases, cardiovascular diseases and osteoporosis." Public Health. Apr. 2008;122(4):417-33.

Kwaik et al., "Microbial quest for food in vivo: 'nutritional virulence' as an emerging paradigm." Cell Microbiol. Jun. 2013;15(6):882-90.

Ledder et al., "Coaggregation between and among human intestinal and oral bacteria." FEMS Microbiol Ecol. Dec. 2008;66(3):630-6.

Lewis et al., "Riddle of biofilm resistance." Antimicrob Agents Chemother. Apr. 2001;45(4):999-1007.

Liu et al., "Environmental and growth phase regulation of the *Streptococcus gordonii* arginine deiminase genes." Appl Environ Microbiol. Aug. 2008;74(16):5023-30.

Liu et al., "Progress toward understanding the contribution of alkali generation in dental biofilms to inhibition of dental caries." Int J Oral Sci. Sep. 2012;4(3):135-40.

Marsh et al., "Dental plaque biofilms: communities, conflict and control." Periodontol 2000. Feb. 2011;55(1):16-35.

Min et al., "Coaggregation by the freshwater bacterium Sphingomonas natatoria alters dual-species biofilm formation." Appl Environ Microbiol. Jun. 2009;75(12):3987-97.

Min et al., "Physicochemical parameters influencing coaggregation between the freshwater bacteria Sphingomonas natatoria 2.1 and Micrococcus luteus 2.13." Biofouling. Nov. 2010;26(8):931-40.

Nagata et al., "Inhibitory effect of human plasma and saliva on co-aggregation between Bacteroides gingivalis and *Streptococcus mitis*." J Dent Res. Aug. 1990;69(8):1476-9.

Nascimento et al., "Correlations of oral bacterial arginine and urea catabolism with caries experience." Oral Microbiol Immunol. Apr. 2009;24(2):89-95.

Nuxoll et al., "CcpA regulates arginine biosynthesis in *Staphylococcus aureus* through repression of proline catabolism." PLoS Pathog. 2012;8(11):e1003033.

Parsek et al., "Bacterial biofilms: an emerging link to disease pathogenesis." Annu Rev Microbiol. 2003;57:677-701.

Petrova et al., "Sticky situations: key components that control bacterial surface attachment." J Bacteriol. May 2012;194(10):2413-25.

Phuong et al., "Involvement of *Acinetobacter* sp. in the floc-formation in activated sludge process." J Biotechnol. Feb. 20, 2012;157(4):505-11.

Reid et al., "Lactobacillus inhibitor production against *Escherichia coli* and coaggregation ability with uropathogens." Can J Microbiol. Mar. 1988;34(3):344-51.

Rickard et al., "Autoinducer 2: a concentration-dependent signal for mutualistic bacterial biofilm growth." Mol Microbiol. Jun. 2006;60(6):1446-56.

Rickard et al., "Bacterial coaggregation: an integral process in the development of multi-species biofilms." Trends Microbiol. Feb. 2003;11(2):94-100.

Rickard et al., "Coaggregation between aquatic bacteria is mediated by specific-growth-phase-dependent lectin-saccharide interactions." Appl Environ Microbiol. Jan. 2000;66(1):431-4.

Rickard et al., "Coaggregation between freshwater bacteria within biofilm and planktonic communities." FEMS Microbiol Lett. Mar. 14, 2003;220(1):133-40.

Rickard et al., "Influence of growth environment on coaggregation between freshwater biofilm bacteria." J Appl Microbiol. 2004;96(6):1367-73.

Rickard et al., "Phylogenetic relationships and coaggregation ability of freshwater biofilm bacteria." Appl Environ Microbiol. Jul. 2002;68(7):3644-50.

| Nutrient source | CFS | CFS+0.5 µM LAHCl | CFS+5 µM LAHCl | CFS+50 µM LAHCl | CFS+500 µM LAHCl | CFS+5 mM LAHCl | CFS+50 mM LAHCl | CFS+500 mM LAHCl |
|---|---|---|---|---|---|---|---|---|
| Viability (% alive) | 85.71 (4.63) | 86.13 (2.43) | 84.83 (3.41) | 86.31 (2.76) | 84.16 (2.98) | 83.88 (4.31) | 83.25 (1.92)* | 67.99 (6.02)** |

| Biofilm treatment | H₂O | 0.05% CPC | 0.01% CPC | 0.05%CPC/500mM LAHCl | 0.01%CPC/500mM LAHCl | H₂O/500mM LAHCl |
|---|---|---|---|---|---|---|
| Biomass (µM³/µM²) | 2.59 (2.26) | 2.61 (1.32) | 2.12 (2.46) | 1.16 (0.68)*,††  | 0.77 (0.39)**,††  | 0.53 (0.51)**,† |
| Thickness (µM) | 3.62 (3.78)  ††  | 2.87 (1.91) † | 1.59 (1.68)*  | 1.01 (0.64)*,† | 0.71 (0.37)**,†  | 0.58 (0.59)**,† |
| Roughness | 1.64 (0.19) | 1.55 (0.16) | 1.69 (0.18)*  | 1.17 (0.14) | 1.78 (0.08)** | 1.86 (0.08)**,†† |
| Viability (% alive) | 84.68 (5.86)  ††  | 15.49 (10.49),† | 30.08 (25.89)  | 15.06 (6.35),† | 12.21 (7.35),†† | 75.54 (6.89)**,†† | ns, antimicrobial agents, inhibiting microbial attachment, inhibiting biofilm growth by removing essential nutrients and promoting biomass detachment and degradation of biofilm matrix (Chen XS, P. S.: Biofilm removal caused by chemical treatments. Water Res 2000; 34:4229-4233; herein incorporated by reference in its entirety). However, such classical removal or disruption methods are not efficacious or feasible in all situations where biofilm formation is undesirable.

COMPOSITIONS AND METHOD FOR DESTABILIZING, ALTERING, AND DISPERSING BIOFILMS

CROSS REFERENCE TO RELATED APPLICATIONS

The present application is a continuation of U.S. patent application Ser. No. 15/023,111, filed Mar. 18, 2016, which is a 371 U.S. National Phase Entry of pending International Application No. PCT/US2014/057235, filed Sep. 24, 2014, which claims priority to U.S. Provisional Application Ser. No. 61/881,762, filed Sep. 24, 2013 and U.S. Provisional Application Ser. No. 61/972,920, filed Mar. 31, 2014, each of which are herein incorporated by reference in their entireties.

FIELD OF INVENTION

The present disclosure relates to compositions and methods for destabilizing biofilms, altering biofilm 3D structure, and dispersing biofilms, in order to enhance biofilm cell removal and/or sensitivity to other agents (e.g., environmental or co-applied treatments). In particular, the present disclosure relates to the use of L-arginine in the removal and/or sensitization (e.g., to antimicrobials) of microorganisms in medical, industrial, domestic, or environmental applications, as well as treatment of bacterial infections (e.g., in biofilms).

BACKGROUND OF THE INVENTION

A biofilm is a well-organized community of microorganisms that adheres to surfaces and is embedded in slimy extracellular polymeric substances (EPSs). EPS is a complex mixture of high-molecular-mass polymers (>10,000 Da) generated by the bacterial cells, cell lysis and hydrolysis products, and organic matter adsorbed from the substrate. EPSs are involved in the establishment of stable arrangements of microorganisms in biofilms (Wolfaardt et al. (1998) Microb. Ecol. 35:213-223; herein incorporated by reference in its entirety), and extracellular DNA (eDNA) is one of the major components of EPSs (Flemming et al. (2001) Water Sci. Technol. 43:9-16; Spoering et al. (2006) Curr. Opin. Microbiol. 9:133-137; each herein incorporated by reference in its entirety). Bacteria living in a biofilm usually have significantly different properties from free-floating (planktonic) bacteria of the same species, as the dense and protected environment of the film allows them to cooperate and interact in various ways. One benefit of this environment is increased resistance to detergents and antibiotics, as the dense extracellular matrix and the outer layer of cells protect the interior of the community. In some cases antibiotic resistance can be increased a thousand-fold (Stewart et al. (2001) Lancet 358:135-138; herein incorporated by reference in its entirety). Biofilms can be formed in various bacterial species (e.g., *Acinetobacter* sp. (e.g., *A. baylyi, A. baumannii*), *Staphylococcus aureus, Stenotrophomonas maltophilia, Escherichia coli* (e.g., *E. coli* K-12). The formation of biofilms by such species is a major determinant of medical outcome during the course of colonization or infection. For example, *Acinetobacter* spp. frequently colonize patients in clinical settings through formation of biofilms on ventilator tubing, on skin and wound sites, medical tubing, and the like, and are a common cause of nosocomial pneumonia.

As biofilms are complex structures formed of various elements, their removal or disruption traditionally requires the use of dispersants, surfactants, detergents, enzyme formulations, antibiotics, biocides, boil-out procedures, corrosive chemicals, mechanical cleaning, use of antimicrobial agents, inhibiting microbial attachment, inhibiting biofilm growth by removing essential nutrients and promoting biomass detachment and degradation of biofilm matrix (Chen XS, P. S.: Biofilm removal caused by chemical treatments. Water Res 2000; 34:4229-4233; herein incorporated by reference in its entirety). However, such classical removal or disruption methods are not efficacious or feasible in all situations where biofilm formation is undesirable.

Additional methods for undesirable bacteria in biofilms are needed.

SUMMARY OF THE INVENTION

The present disclosure relates to compositions and methods for destabilizing biofilms, altering biofilm 3D structure, and dispersing biofilms, in order to enhance biofilm cell removal and/or sensitivity to other agents (e.g., environmental or co-applied treatments). In particular, the present disclosure relates to the use of L-arginine in the removal and/or sensitization (e.g., to antimicrobials) of microorganisms in medical, industrial, domestic, or environmental applications, as well as treatment of bacterial infections (e.g., in biofilms).

Embodiments of the present invention provide compositions (e.g., pharmaceutical, commercial, health care, etc.), systems, uses, and methods that result in one or more of: inducing cell-damage, killing cells, disrupting intra-cellular processes leading to deregulation/loss of homeostasis, disrupting cell-cell adhesion, inducing three dimensional rearrangement of architecture, disrupting cell-cell signaling, disrupting cell-cell metabolic interactions, disrupting adhesion to surfaces, reducing the pathogenic potential of biofilms, reducing biofilm mass, decreasing the proportion of pathogenic bacteria in a biofilm, increasing the proportion of beneficial bacteria in a biofilm, or preventing growth of a microorganism in a biofilm, comprising: contacting bacteria in a biofilm with cell-free L-arginine at a concentration of at least 1 mM, wherein the contacting kills or inhibits the growth of microorganisms and/or alters the 3D arrangement of the cells in the biofilm, which can damage bacteria by preventing them from interacting with others and/or exposing them to deleterious environmental effects. In some embodiments, the microorganism is a bacterium. In some embodiments, the bacteria are in a coaggregate. In some embodiments, the biofilm is a dental biofilm. In some embodiments, the bacteria are in a coaggregate or biofilm with a plurality of different bacterial species (e.g., of *Streptococcus* and *Actinomyces*, such as, for example, *S. gordonii* and *A. oris*). In some embodiments, the L-arginine prevents coaggregation or promotes de-adhesion/dispersion of said bacteria. In some embodiments, the L-arginine is present at a concentration of at least 1 mM (e.g., at least 10 mM, at least 50 mM, at least 100 mM, 200 mM, at least 250 mM, at least 300 mM, at least 350 mM, at least 400 mM, at least 450 mM, at least 500 mM, at least 600 mM, at least 700 mM, at least 800 mM, at least 900 mM, or at least 1 M). In some embodiments, the bacteria are in multi-species oral biofilms (e.g., dental plaque in saliva). In some embodiments, L-arginine disrupts biofilms grown in saliva without antimicrobial activity. In some embodiments, the method further comprises contacting the bacteria with cetylpyridinium chloride (CPC).

Additional embodiments comprise the use of a composition comprising L-arginine at a concentration of at least 1 mM to induce one or more of: inducing microbial cell-damage, killing cells, disrupting intra-cellular processes leading to deregulation/loss of homeostasis, disrupting cell-cell adhesion, inducing three dimensional rearrangement of architecture, disrupting cell-cell signaling, disrupting cell-cell metabolic interactions, disrupting adhesion to surfaces, reducing the pathogenic potential of biofilms, reducing biofilm mass, decreasing the proportion of pathogenic bacteria in a biofilm, increasing the proportion of beneficial bacteria in a biofilm, or preventing growth of a microorganism in a biofilm. In some embodiments, the composition further comprises at cetylpyridinium chloride (CPC).

Further embodiments provide a plasmid that reports expression or concentration of a component of a biofilm or planktonic cell population, where the plasmid comprises either a first marker under the control of a constitutive promoter or a second marker under the control of a promoter induced by the component. In some embodiments, the marker is a fluorescent marker (e.g., GFP or Mcherry). In some embodiments, the first promoter is a streptococcal ribosomal promoter (e.g., a S. gordonii DL1 50S ribosomal protein (SGO_1192) promoter). In some embodiments, the second promoter is S. gordonii catabolite control protein A (SGO_0773), or S. gordonii argC or arcA promoter.

Additional embodiments provide a streptococcal cell (e.g., S. gordonii) comprising the plasmid. In some embodiments, the cell is in a biofilm.

Some embodiments provide methods and uses of monitoring concentration of a component (e.g., arginine or AI-2) of a biofilm or planktonic cell culture, comprising: a) contacting a streptococcal cell with the plasmid described herein; and b) measuring the level of the marker. In some embodiments, the level of expression of the marker is correlated to the level of the component. In some embodiments, the method further comprises the step of contacting the cell with a test compound (e.g. a drug that kills or inhibits or is suspected of killing or inhibiting the growth of the cell).

Additional embodiments are described herein.

DEFINITIONS

Figure 1:
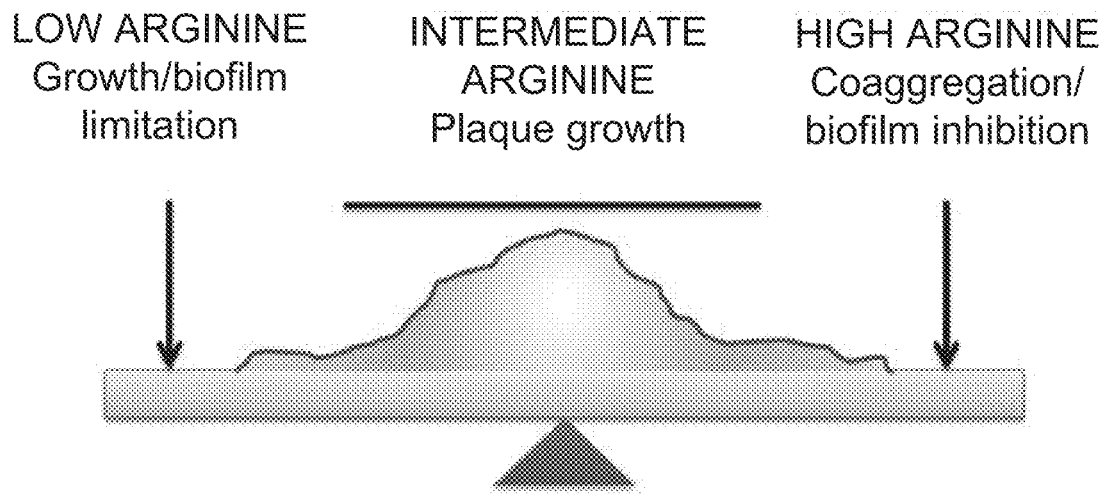
FIG. 1 shows the role of arginine in dental plaque growth. High and low concentrations of L-arginine cause biofilm destabilization and results in many cells to disperse/de-adhere from the biofilm leaving behind dead/damage unresponsive cells.

To facilitate an understanding of the present invention, a number of terms and phrases are defined below:

As used herein the term "biofilm" refers to any three-dimensional, (e.g., matrix-encased) microbial community displaying multicellular characteristics. Accordingly, as used herein, the term biofilm includes surface-associated biofilms as well as biofilms in suspension, such as flocs and granules. Biofilms may comprise a single microbial species or may be mixed species complexes, and may include bacteria as well as fungi, algae, protozoa, or other microorganisms. In some embodiments, biofilms comprise coaggregating organisms. In some embodiments, biofilms comprise a single organism or multiple organisms that do not coaggregate.

As used herein, the term "host cell" refers to any eukaryotic or prokaryotic cell (e.g., bacterial cells such as E. coli, yeast cells, mammalian cells, avian cells, amphibian cells, plant cells, fish cells, and insect cells), whether located in vitro or in vivo. For example, host cells may be located in a transgenic animal.

As used herein, the term "prokaryotes" refers to a group of organisms that usually lack a cell nucleus or any other membrane-bound organelles. In some embodiments, prokaryotes are bacteria. The term "prokaryote" includes both archaea and eubacteria.

As used herein, the term "subject" refers to individuals (e.g., human, animal, or other organism) to be treated by the methods or compositions of the present invention. Subjects include, but are not limited to, mammals (e.g., murines, simians, equines, bovines, porcines, canines, felines, and the like), and most preferably includes humans. In the context of the invention, the term "subject" generally refers to an individual who will receive or who has received treatment for a condition characterized by the presence of biofilm-forming bacteria, or in anticipation of possible exposure to biofilm-forming bacteria.

As used herein the term, "in vitro" refers to an artificial environment and to processes or reactions that occur within an artificial environment. In vitro environments include, but are not limited to, test tubes and cell cultures. The term "in vivo" refers to the natural environment (e.g., an animal or a cell) and to processes or reaction that occur within a natural environment.

As used herein, the term "virulence" refers to the degree of pathogenicity of a microorganism (e.g., bacteria or fungus), e.g., as indicated by the severity of the disease produced or its ability to invade the tissues of a subject. It is generally measured experimentally by the median lethal dose ($LD_{50}$) or median infective dose ($ID_{50}$). The term may also be used to refer to the competence of any infectious agent to produce pathologic effects.

As used herein, the term "effective amount" refers to the amount of a composition (e.g., a composition comprising L-arginine) sufficient to effect beneficial or desired results. An effective amount can be administered in one or more administrations, applications or dosages and is not intended to be limited to a particular formulation or administration route. In some embodiments, the effective amount is at least 1 mM (e.g., 10 mM, 50 mM, 100 mM, 200 mM, 300 mM, 400 mM, 500 mM, 750 mM, 1000 mM or more).

As used herein, the term "administration" refers to the act of giving a drug, prodrug, or other agent, or therapeutic treatment (e.g., compositions comprising L-arginine) to a physiological system (e.g., a subject or in vivo, in vitro, or ex vivo cells, tissues, and organs). Exemplary routes of administration to the human body can be through the eyes (ophthalmic), mouth (oral), skin (transdermal), nose (nasal), lungs (inhalant), oral mucosa (buccal), ear, by injection (e.g., intravenously, subcutaneously, intratumorally, intraperitoneally, etc.), topical administration and the like.

As used herein, the term "treating a surface" refers to the act of exposing a surface to one or more compositions comprising L-arginine. Methods of treating a surface include, but are not limited to, spraying, misting, submerging, and coating.

As used herein, the term "co-administration" refers to the administration of at least two agent(s) (e.g., L-arginine in combination with an antimicrobial agent) or therapies to a subject. In some embodiments, the co-administration of two or more agents or therapies is concurrent. In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s).

As used herein, the term "wound" refers broadly to injuries to tissue including the skin, subcutaneous tissue, muscle, bone, and other structures initiated in different ways, for example, surgery, (e.g., open post cancer resection wounds, including but not limited to, removal of melanoma and breast cancer etc.), contained post-operative surgical wounds, pressure sores (e.g., from extended bed rest) and wounds induced by trauma. As used herein, the term "wound" is used without limitation to the cause of the wound, be it a physical cause such as bodily positioning as in bed sores or impact as with trauma or a biological cause such as disease process, aging process, obstetric process, or any other manner of biological process. Wounds caused by pressure may also be classified into one of four grades depending on the depth of the wound: i) Grade I: wounds limited to the epidermis; ii) Grade II: wounds extending into the dermis; iii) Grade III: wounds extending into the subcutaneous tissue; and iv) Grade IV: wounds wherein bones are exposed (e.g., a bony pressure point such as the greater trochanter or the sacrum). The term "partial thickness wound" refers to wounds that are limited to the epidermis and dermis; a wound of any etiology may be partial thickness. The term "full thickness wound" is meant to include wounds that extend through the dermis.

As used herein, "wound site" refers broadly to the anatomical location of a wound, without limitation.

As used herein, the term "dressing" refers broadly to any material applied to a wound for protection, absorbance, drainage, treatment, etc. Numerous types of dressings are commercially available, including films (e.g., polyurethane films), hydrocolloids (hydrophilic colloidal particles bound to polyurethane foam), hydrogels (cross-linked polymers containing about at least 60% water), foams (hydrophilic or hydrophobic), calcium alginates (nonwoven composites of fibers from calcium alginate), and cellophane (cellulose with a plasticizer) (Kannon and Garrett (1995) *Dermatol. Surg.* 21: 583-590; Davies (1983) *Burns* 10: 94; each herein incorporated by reference). The present invention also contemplates the use of dressings impregnated with pharmacological compounds (e.g., antibiotics, antiseptics, thrombin, analgesic compounds, etc). Cellular wound dressings include commercially available materials such as Apligraf®, Dermagraft®, Biobrane®, TransCyte®, Integra® Dermal Regeneration Template®, and OrCell®.

As used herein, the term "toxic" refers to any detrimental or harmful effects on a subject, a cell, or a tissue as compared to the same cell or tissue prior to the administration of the toxicant.

As used herein, the term "pharmaceutical composition" refers to the combination of an active agent (e.g., L-arginine) with a carrier, inert or active, making the composition especially suitable for diagnostic or therapeutic use in vitro, in vivo or ex vivo.

The terms "pharmaceutically acceptable" or "pharmacologically acceptable," as used herein, refer to compositions that do not substantially produce adverse reactions, e.g., toxic, allergic, or immunological reactions, when administered to a subject.

As used herein, the term "topically" refers to application of the compositions of the present invention to the surface of the skin and mucosal cells and tissues (e.g., alveolar, buccal, lingual, masticatory, or nasal mucosa, and other tissues and cells which line hollow organs or body cavities).

As used herein, the term "pharmaceutically acceptable carrier" refers to any of the standard pharmaceutical carriers including, but not limited to, phosphate buffered saline solution, water, emulsions (e.g., such as an oil/water or water/oil emulsions), and various types of wetting agents, any and all solvents, dispersion media, coatings, sodium lauryl sulfate, isotonic and absorption delaying agents, disintrigrants (e.g., potato starch or sodium starch glycolate), and the like. The compositions also can include stabilizers and preservatives. For examples of carriers, stabilizers, and adjuvants. (See e.g., Martin, Remington's Pharmaceutical Sciences, 15th Ed., Mack Publ. Co., Easton, Pa. (1975), incorporated herein by reference). In certain embodiments, the compositions of the present invention may be formulated for veterinary, horticultural or agricultural use. Such formulations include dips, sprays, seed dressings, stem injections, sprays, and mists. In certain embodiments, compositions of the present invention may be used in any application where it is desirable to alter (e.g., inhibit) the formation of biofilms, e.g., food industry applications; consumer goods (e.g., medical goods, goods intended for consumers with impaired or developing immune systems (e.g., infants, children, elderly, consumers suffering from disease or at risk from disease), and the like.

As used herein, the term "medical devices" includes any material or device that is used on, in, or through a subject's or patient's body, for example, in the course of medical treatment (e.g., for a disease or injury). Medical devices include, but are not limited to, such items as medical implants, wound care devices, drug delivery devices, and body cavity and personal protection devices. The medical implants include, but are not limited to, urinary catheters, intravascular catheters, dialysis shunts, wound drain tubes, skin sutures, vascular grafts, implantable meshes, intraocular devices, heart valves, and the like. Wound care devices include, but are not limited to, general wound dressings, biologic graft materials, tape closures and dressings, and surgical incise drapes. Drug delivery devices include, but are not limited to, needles, drug delivery skin patches, drug delivery mucosal patches and medical sponges. Body cavity and personal protection devices, include, but are not limited to, tampons, sponges, surgical and examination gloves, contact lenses, and toothbrushes. Birth control devices include, but are not limited to, intrauterine devices (IUDs), diaphragms, and condoms.

As used herein, the term "therapeutic agent," refers to compositions that decrease the infectivity, morbidity, or onset of mortality in a subject (e.g., a subject contacted by a biofilm-forming microorganism) or that prevent infectivity, morbidity, or onset of mortality in a host contacted by a biofilm-forming microorganism. As used herein, therapeutic agents encompass agents used prophylactically, e.g., in the absence of a biofilm-forming organism, in view of possible future exposure to a biofilm-forming organism. Such agents may additionally comprise pharmaceutically acceptable compounds (e.g., adjuvants, excipients, stabilizers, diluents, and the like). In some embodiments, the therapeutic agents of the present invention are administered in the form of topical compositions, injectable compositions, ingestible compositions, and the like. When the route is topical, the form may be, for example, a solution, cream, ointment, salve or spray.

As used herein, the term "pathogen" refers to a biological agent that causes a disease state (e.g., infection, cancer, etc.) in a host. "Pathogens" include, but are not limited to, viruses, bacteria, archaea, fungi, protozoans, mycoplasma, prions, and parasitic organisms.

As used herein, the term "microbe" refers to a microorganism and is intended to encompass both an individual organism, or a preparation comprising any number of the organisms.

As used herein, the term "microorganism" refers to any species or type of microorganism, including but not limited to, bacteria, archaea, fungi, protozoans, mycoplasma, and parasitic organisms.

As used herein, the term "fungi" is used in reference to eukaryotic organisms such as the molds and yeasts, including dimorphic fungi.

The terms "bacteria" and "bacterium" refer to all prokaryotic organisms, including those within all of the phyla in the Kingdom Procaryotae. It is intended that the term encompass all microorganisms considered to be bacteria including *Mycoplasma, Chlamydia, Actinomyces, Streptomyces,* and *Rickettsia*. All forms of bacteria are included within this definition including cocci, bacilli, spirochetes, spheroplasts, protoplasts, etc. Also included within this term are prokaryotic organisms that are Gram-negative or Gram-positive. "Gram-negative" and "Gram-positive" refer to staining patterns with the Gram-staining process, which is well known in the art. (See e.g., Finegold and Martin, Diagnostic Microbiology, 6th Ed., CV Mosby St. Louis, pp. 13-15 (1982)). "Gram-positive bacteria" are bacteria that retain the primary dye used in the Gram-stain, causing the stained cells to generally appear dark blue to purple under the microscope. "Gram-negative bacteria" do not retain the primary dye used in the Gram-stain, but are stained by the counterstain. Thus, Gram-negative bacteria generally appear red.

The term "non-pathogenic bacteria" or "non-pathogenic bacterium" includes all known and unknown non-pathogenic bacterium (Gram-positive or Gram-negative) and any pathogenic bacterium that has been mutated or converted to a non-pathogenic bacterium. Furthermore, a skilled artisan recognizes that some bacteria may be pathogenic to specific species and non-pathogenic to other species; thus, these bacteria can be utilized in the species in which it is non-pathogenic or mutated so that it is non-pathogenic.

As used herein, the term "non-human animals" refers to all non-human animals including, but are not limited to, vertebrates such as rodents, non-human primates, ovines, bovines, ruminants, lagomorphs, porcines, caprines, equines, canines, felines, aves, etc.

As used herein, the term "cell culture" refers to any in vitro culture of cells, including, e.g., prokaryotic cells and eukaryotic cells. Included within this term are continuous cell lines (e.g., with an immortal phenotype), primary cell cultures, transformed cell lines, finite cell lines (e.g., non-transformed cells), bacterial cultures in or on solid or liquid media, and any other cell population maintained in vitro.

The term "coating" as used herein refers to a layer of material covering, e.g., a medical device or a portion thereof. A coating can be applied to the surface or impregnated within the material of the implant.

As used herein, the term "antimicrobial agent" refers to composition that decreases, prevents or inhibits the growth of bacterial and/or fungal organisms. Examples of antimicrobial agents include, e.g., antibiotics and antiseptics.

The term "antiseptic" as used herein is defined as an antimicrobial substance that inhibits the action of microorganisms, including but not limited to α-terpineol, methylisothiazolone, cetylpyridinium chloride, chloroxyleneol, hexachlorophene, chlorhexidine and other cationic biguanides, methylene chloride, iodine and iodophores, triclosan, taurinamides, nitrofurantoin, methenamine, aldehydes, azylic acid, silver, benzyl peroxide, alcohols, and carboxylic acids and salts. One skilled in the art is cognizant that these antiseptics can be used in combinations of two or more to obtain a synergistic or additive effect. Some examples of combinations of antiseptics include a mixture of chlorhexidine, chlorhexidine and chloroxylenol, chlorhexidine and methylisothiazolone, chlorhexidine and (α-terpineol, methylisothiazolone and α-terpineol; thymol and chloroxylenol; chlorhexidine and cetylpyridinium chloride; or chlorhexidine, methylisothiazolone and thymol. These combinations provide a broad spectrum of activity against a wide variety of organisms.

The term "antibiotics" as used herein is defined as a substance that inhibits the growth of microorganisms, preferably without damage to the host. For example, the antibiotic may inhibit cell wall synthesis, protein synthesis, nucleic acid synthesis, or alter cell membrane function.

Classes of antibiotics include, but are not limited to, macrolides (e.g., erythromycin), penicillins (e.g., nafcillin), cephalosporins (e.g., cefazolin), carbapenems (e.g., imipenem), monobactam (e.g., aztreonam), other beta-lactam antibiotics, beta-lactam inhibitors (e.g., sulbactam), oxalines (e.g. linezolid), aminoglycosides (e.g., gentamicin), chloramphenicol, sufonamides (e.g., sulfamethoxazole), glycopeptides (e.g., vancomycin), quinolones (e.g., ciprofloxacin), tetracyclines (e.g., minocycline), fusidic acid, trimethoprim, metronidazole, clindamycin, mupirocin, rifamycins (e.g., rifampin), streptogramins (e.g., quinupristin and dalfopristin) lipoprotein (e.g., daptomycin), polyenes (e.g., amphotericin B), azoles (e.g., fluconazole), and echinocandins (e.g., caspofungin acetate).

Examples of specific antibiotics include, but are not limited to, erythromycin, nafcillin, cefazolin, imipenem, aztreonam, gentamicin, sulfamethoxazole, vancomycin, ciprofloxacin, trimethoprim, rifampin, metronidazole, clindamycin, teicoplanin, mupirocin, azithromycin, clarithromycin, ofloxacin, lomefloxacin, norfloxacin, nalidixic acid, sparfloxacin, pefloxacin, amifloxacin, gatifloxacin, moxifloxacin, gemifloxacin, enoxacin, fleroxacin, minocycline, linezolid, temafloxacin, tosufloxacin, clinafloxacin, sulbactam, clavulanic acid, amphotcricin B, fluconazole, itraconazole, ketoconazole, and nystatin. Other examples of antibiotics, such as those listed in Sakamoto et al, U.S. Pat. No. 4,642,104 herein incorporated by reference will readily suggest themselves to those of ordinary skill in the art.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Such examples are not however to be construed as limiting the sample types applicable to the present invention.

DETAILED DESCRIPTION OF THE INVENTION

The present disclosure relates to compositions and methods for destabilizing biofilms, altering biofilm 3D structure, and dispersing biofilms, in order to enhance biofilm cell removal and/or sensitivity to other agents (e.g., environmental or co-applied treatments). In particular, the present disclosure relates to the use of L-arginine in the removal and/or sensitization (e.g., to antimicrobials) of microorganisms in medical, industrial, domestic, or environmental applications, as well as treatment of bacterial infections (e.g., in biofilms).

A biofilm is an aggregate of microorganisms in which cells adhere to each other and/or to a surface. These adherent cells are frequently embedded within a self-produced matrix of extracellular polymeric substance (EPS). Biofilm EPS, also referred to as slime, is a polymeric conglomeration generally composed of extracellular DNA, proteins, and polysaccharides in various configurations and of various compositions. Biofilms may form on living or non-living surfaces, and represent a prevalent mode of microbial life in natural, industrial and clinical settings. The microbial cells growing in a biofilm are physiologically distinct from planktonic cells of the same organism, which, by contrast, are single cells that may float or swim in a liquid medium.

Microbial biofilms form in response to many factors including but not limited to cellular recognition of specific or non-specific attachment sites on a surface, nutritional cues, or in some cases, by exposure of planktonic cells to sub-inhibitory concentrations of antibiotics. When a cell switches to the biofilm mode of growth, it undergoes a phenotypic shift in behavior in which large suites of genes are differentially regulated (Petrova et al., J. Bacteriol. 2012 May; 194(10):2413-25; Stoodley et al., Annu Rev Microbiol. 2002; 56:187-209).

Although the present invention is not limited by any type of biofilm, biofilm formation typically begins with the attachment of free-floating microorganisms to a surface. These first colonists adhere to the surface initially through weak, reversible Van der Waals forces. If the colonists are not immediately separated from the surface, they can anchor themselves more permanently using cell adhesion structures such as pili.

Initial colonists commonly facilitate the arrival of other cells by providing more diverse adhesion sites and beginning to build the matrix that holds the biofilm together. Some species are not able to attach to a surface on their own but are often able to anchor themselves to the matrix or directly to earlier colonists. It is during this colonization that the cells are able to communicate via quorum sensing, for example, using such compounds as N-acyl homoserine lactone (AHL). Once colonization initiates, the biofilm grows through a combination of cell division and recruitment. The final stage of biofilm formation is known as development although herein the terms "formation" and "development" are used interchangeably. In this final stage, the biofilm is established and may only change in shape and size. The development of a biofilm may allow for an aggregate cell colony (or colonies) to be increasingly antibiotic resistant.

Dispersal of cells from the biofilm colony is an essential stage of the biofilm lifecycle. Dispersal enables biofilms to spread and colonize new surfaces. Enzymes that degrade the biofilm extracellular matrix, such as dispersin B and deoxyribonuclease, may play a role in biofilm dispersal (Whitchurch et al. (2002) Science 295:1487; herein incorporated by reference in its entirety). Biofilm matrix degrading enzymes may be useful as anti-biofilm agents (Kaplan et al. (2004) Antimicrobial Agents and Chemotherapy 48 (7): 2633-6; Xavier et al. (2005) Microbiology 151 (Pt 12): 3817-32; each herein incorporated by reference in its entirety). A fatty acid messenger, cis-2-decenoic acid, can induce dispersion and inhibit growth of biofilm colonies. Secreted by *Pseudomonas aeruginosa*, this compound induces dispersion in several species of bacteria and the yeast *Candida albicans* (Davies et al. (2009) Journal of Bacteriology 191 (5): 1393-403; herein incorporated by reference in its entirety).

Biofilms are ubiquitous and are usually found on solid substrates submerged in or exposed to some aqueous solution, although they can form as floating mats on liquid surfaces and also on the surface of leaves, particularly in high humidity climates. Given sufficient resources for growth, a biofilm will quickly grow to be macroscopic. Many types of microbes can form biofilms, e.g., bacteria, archaea, protozoa, fungi and algae. Biofilms may comprise a single type of microbe (monospecies biofilms), or, commonly, multiple types. In some mixed species biofilms, each group performs specialized metabolic functions.

Biofilms form in environments including but not limited to: substrates (e.g., rocks, pebbles) in natural bodies of water (e.g., rivers, pools, streams, oceans, springs); extreme environments (e.g., hot springs including waters with extremely acidic or extremely alkaline pH; frozen glaciers); residential and industrial settings in which solid surfaces are exposed to liquid (e.g., showers, water and sewage pipes, floors and counters in food preparation or processing areas, water-cooling systems, marine engineering systems); hulls and interiors of marine vessels; sewage and water treatment facilities (e.g., water filters, pipes, holding tanks); contaminated waters; within or upon living organisms (e.g., dental plaque, surface colonization or infection of e.g., skin, surfaces of tissues or organs or body cavities or at wound sites; plant epidermis, interior of plants); on the inert surfaces of implanted devices such as catheters, prosthetic cardiac valves, artificial joints, and intrauterine devices; and the like.

Biofilms are involved in a wide variety of microbial infections in the body. Infectious processes in which biofilms have been implicated include but are not limited to urinary tract infections, catheter infections, middle-ear infections, formation of dental plaque and gingivitis, contact lens contamination (Imamura et al. (2008) Antimicrobial Agents and Chemotherapy 52 (1): 171-82; herein incorporated by reference in its entirety), and less common but more lethal processes such as endocarditis, infections in cystic fibrosis, and infections of permanent indwelling devices such as joint prostheses and heart valves (Lewis et al. (2001) *Antimicrobial Agents and Chemotherapy* 45 (4): 999-1007; Parsek et al. (2003) Annual Review of Microbiology 57: 677-701; each herein incorporated by reference in its entirety). Bacterial biofilms may impair cutaneous wound healing and reduce topical antibacterial efficiency in healing or treating infected skin wounds (Davis et al. (2008) Wound Repair and Regeneration 16 (1): 23-9; herein incorporated by reference in its entirety).

Coaggregation is the highly specific recognition and adhesion of genetically distinct bacteria mediated by complementary protein adhesins and polysaccharide receptors on the cell surface of coaggregating cells (Kolenbrander, Annu Rev Microbiol 54, 413-437, 2000; Rickard et al., Trends Microbiol 11, 94-100, 2003a). This phenomenon is distinct from autoaggregation, which is the recognition and adhesion of genetically identical bacteria to one another (Khemaleelakul et al., J Endod 32, 312-318, 2006; Rickard et al., FEMS Microbiol Lett 220, 133-140, 2003b; Van Houdt & Michiels, Res Microbiol 156, 626-633, 2005). Coaggregation was first described between human dental plaque bacteria in 1970 (Gibbons & Nygaard, Arch Oral Biol 15, 1397-1400, 1970), and work over the last two decades has shown that it also occurs between bacteria isolated from the human gut, the human urogenital tract, in wastewater flocs, and freshwater biofilms (Ledder et al., FEMS Microbiol Ecol 66, 630-636, 2008; Phuong et al., J Biotechnol, 2011; Reid et al., Can J Microbiol 34, 344-351, 1988; Rickard et al., Appl Environ Microbiol 66, 431-434, 2000; Simoes et al., Appl Environ Microbiol 74, 1259-1263, 2008). Coaggregation has also been shown to occur among numerous taxonomically distinct freshwater species (Rickard et al., Appl Environ Microbiol 68, 3644-3650, 2002; Rickard et al., 2003b, supra; Rickard et al., Appl Environ Microbiol 70, 7426-7435, 2004b; Simoes et al., Appl Environ Microbiol 74, 1259-1263, 2008) and in planktonic and biofilm populations (Rickard et al., J Appl Microbiol 96, 1367-1373, 2004a). Studies of coaggregation between *Sphingomonas* (*Blastomonas*) *natatoria* and *Micrococcus luteus* demonstrated that the ability of a species to coaggregate alters dual-species biofilm development in both flowing and static environments (Min & Rickard, Appl Environ Microbiol 75, 3987-3997, 2009; Min et al., Biofouling 26, 931-940, 2010). Coaggregation may mediate biofilm development, architectural changes, and alterations in the species composition (Hojo et al., J Dent Res 88, 982-990, 2009; Kolenbrander et al., Periodontol 2000 42, 47-79, 2006; Rickard et al., 2003a, supra). In addition, coaggregation may play a role in promoting or hindering the integration of pathogenic species into freshwater biofilms (Buswell et al., Appl Environ Microbiol 64, 733-741, 1998). Evidence to support such a possibility can be found in studies of dental plaque biofilms where coaggregation has been indicated to promote the integration of oral pathogens such as *Porphyromonas gingivalis* (Kolenbrander et al., Periodontol 2000 42, 47-79, 2006; Whitmore & Lamont, Mol Microbiol 81, 305-314, 2011).

Dental plaque is composed of hundreds of species of bacteria that can collectively cause oral and systemic diseases (Jakubovics et al., Oral diseases. 2010; 16(8):729-39; Kuo et al., Public Health. 2008; 122(4):417-33.). During dental plaque development, bacteria sense and respond to numerous exogenous bacterial- or environmental-derived chemicals which alter their ability to establish themselves within these biofilms.

Oral biofilms cause major problems throughout both industrialized and developing countries. Data from recent surveys indicate that 23.7% of US adults have untreated dental caries while 38.5% of adults have moderate to severe periodontitis (National Center for Health Statistics. Health, United States, 2011: With Special Feature on Socioeconomic Status and Health. Hyattsville, Md.: 2012; Eke et al., Journal of dental research. 2012; 91(10):914-20). Untreated dental caries also affects between 15-20% of children up to 19 years, while periodontitis is a major problem in the elderly population, where 64% of adults over 65 years have moderate to severe forms of the condition (National Center for Health Statistics. Health, United States, 2011: With Special Feature on Socioeconomic Status and Health. Hyattsville, Md.: 2012; Eke et al., Journal of dental research. 2012; 91(10):914-20). Clearly, new methods for controlling dental plaque-related diseases are urgently needed.

Dental plaque is a finely balanced homeostatic bacterial community (Marsh et al., Periodontology 2000. 2011; 55(1): 16-35). Embodiments of the present invention provide a broad-acting intervention that alters the balance of such oral bacterial communities and is more effective at controlling dental plaque-related diseases than strategies that target individual species. Dental plaque contains an interactive "aware" community of microbes. On cleaned tooth-surfaces, dental plaque develops through a microbial succession (Jakubovics et al, supra; Kolenbrander et al., Nature reviews Microbiology. 2010; 8(7):471-80; Kolenbrander et al., Periodontology 2000. 2006; 42:47-79 23, 24). Initial colonizers, predominantly *Streptococcus* species, adhere to salivary pellicle and produce thin layers of biofilm that support the integration of other species through coaggregation, cell-cell signalling, and metabolite recognition (Jakubovics et al, supra; Kolenbrander et al., Nature reviews Microbiology. 2010; 8(7):471-80; Hojo et al., Journal of dental research. 2009; 88(11):982-90; Rickard et al., Trends Microbiol. 2003; 11(2):94-100; Bowden et al., Advances in dental research. 1997; 11(1):81-99). Coaggregation involves specific recognition and adhesion between bacteria and brings different species in close proximity. This increases the potential to exchange cell-cell signalling molecules or metabolites (Kolenbrander et al., Nature reviews Microbiology. 2010; 8(7):471-80; Hojo et al., supra). For example, the signalling molecule autoinducer-2 (AI-2)mediates mutualistic growth of the coaggregating partners *Streptococcus oralis* and *Actinomyces oris*, and facilitates the development of biofilms containing the coaggregating partners *S. gordonii* and *S. oralis* (Cuadra-Saenz et al., Microbiology. 2012; 158(Pt 7):1783-95; Rickard et al., Molecular microbiology. 2006; 60(6):1446-56.). Examples of important metabolites include hydrogen peroxide, which is produced by some streptococci, and inhibits other species including mutans streptococci (Zhu et al., Oxid Med Cell Longev. 2012; 2012:717843), and lactate which is produced by streptococci and used by coaggregating *Veillonella* species for energy (Egland et al., Proceedings of the National Academy of Sciences of the United States of America. 2004; 101(48): 16917-22). Arginine is important in metabolite exchange (Jakubovics et al., supra) but, unlike other mechanisms of communication, it also disrupts coaggregation between oral bacteria and appears to have a major impact upon biofilm structure (Edwards et al., Oral microbiology and immunology. 2007; 22(4):217-24; Sato et al., J Microbiol Immunol Infect. 2012; Ellen et al., Oral microbiology and immunology. 1992; 7(4):198-203.).

Thus, arginine, although receiving limited attention to date, is a key global moderator of biofilm development and a pivotal component in the onset of caries or periodontal disease (Nascimento et al., Oral microbiology and immunology. 2009; 24(2):89-95). The concept of 'nutritional virulence', whereby bacterial systems for acquiring nutrients from the host are considered key factors for pathogenesis, is emerging as an important paradigm for infectious diseases (Abu Kwaik et al., Cellular microbiology. 2013; 15(6):882-90). Amino acids in particular are often a growth-limiting resource for bacteria. Even when species possess all the genes required for amino acid biosynthesis, they may be functionally auxotrophic in certain conditions. For example, *Staphylococcus aureus* possesses the full genetic pathway encoding the biosynthesis of L-arginine from L-glutamate, yet cannot grow in vitro without L-arginine (Nuxoll et al., PLoS pathogens. 2012; 8(11):e1003033). Similarly, *S. gordonii* can biosynthesize L-arginine anaerobically but is a functional arginine auxotroph in aerobic conditions (Jakubovics et al., supra). Oral streptococci have varied requirements for amino acids in vitro (Cowman et al., Applied microbiology. 1975; 30(3):374-80; Cowman et al., Journal of dental research. 1978; 57(1):48; Terleckyj et al., Infect Immun. 1975; 11(4):656-64), and it is not well understood how these nutritional deficiencies restrict growth in dental plaque. Early colonizing bacteria obtain most of their nutrients from saliva (Bowden et al., Advances in dental research. 1997; 11(1):81-99). Human saliva can contain up to 40 μM free arginine (Van Wuyckhuyse et al., Journal of dental research. 1995; 74(2):686-90). *S. gordonii* is unable to grow aerobically in <25 μM L-arginine (Jakubovics et al., supra). Arginine restriction of *S. gordonii* growth can be overcome by coaggregation with *A. oris* (Jakubovics et al., supra). Expression of *S. gordonii* arginine biosynthesis genes is strongly down-regulated in coaggregates compared with monocultures, indicating that coaggregation relieves low-arginine stress. Further, coaggregation with *A. oris* supported growth of *S. gordonii* under arginine-limited conditions. Therefore, inter-bacterial interactions are important for growth in saliva.

1. Therapeutic Methods

Experiments conducted during the course of development of embodiments of the present disclosure demonstrated that high concentrations of arginine abrogate biofilm formation by *S. gordonii*. Biofilm formation was highly sensitive to millimolar levels of arginine in a dose-dependent manner.

Arginine concentrations in saliva are thought to stay low due to continuous uptake into cells and turnover by bacterial arginine deiaminase systems (ADS's), which catabolise arginine to ATP, ammonia and L-glutamine (Van Wuyckhuyse et al., Journal of dental research. 1995; 74(2):686-90). The production of ammonia increases the local pH of plaque, which protects against caries (Liu et al., International journal of oral science. 2012; 4(3):135-40.). The ADS's of the opportunistic pathogens *Pseudomonas aeruginosa* and *S. aureus* are up-regulated in biofilms and these systems are essential to protect cells from oxygen and glycolysis-derived acids (39, 40). The ADS's of oral streptococci have been shown to influence biofilm formation in mixed-species systems, where removal of L-arginine by *S. intermedius* ADS inhibits biofilm formation by the periodontal pathogen *P. gingivalis* (Cugini et al., Microbiology. 2013; 159(Pt 2):275-85). Production of ADS's is controlled at the level of transcription by ArgR/AhrC family regulators such as ArcR (Liu et al., Applied and environmental microbiology. 2008; 74(16):5023-30; Zeng et al., Journal of bacteriology. 2006; 188(3):941-9). ArcR is important for *S. gordonii* biofilm formation in nutrient-rich growth media.

Further experiments described herein demonstrated that L-arginine reduces the pathogenic potential of biofilms by reducing the biofilm biomass and reducing the total amount and proportion of pathogens (e.g., without direct antimicrobial activity); and L-arginine augments/enhances the activity of antimicrobials such as CPC. This is through enhancing access of antimicrobial by loosening biofilm and also by altering the growth-rate of the bacteria; L-arginine causes cell-cell signaling dysregulation; L-arginine is a combinational treatment that up-regulates metabolism, alters cell-cell signaling, and inhibits cell-cell adhesion; and L-arginine increases the proportion of beneficial bacteria that can combat the negative effects of potential pathogens such as *S. mutans*.

Accordingly, embodiments of the present invention provide compositions (e.g., pharmaceutical or research compositions or kits) comprising L-arginine (e.g., alone or in combination with CPC) and pharmaceutical, industrial, or research methods of using L-arginine in the treatment and prevention of bacterial infections (e.g., dental plaque) and in decontamination of surfaces (e.g., surfaces of medical devices).

In some embodiments, the present disclosure provides compositions and methods for using L-arginine to disrupt cell-cell interactions (adhesion) within a biofilm, disrupt bacterial homeostasis, induce cell-damage and killing, disrupt intra-cellular processes leading to deregulation/loss of homeostasis, disrupt cell-cell adhesion in biofilms, biofilm 3D rearrangement of architecture, disrupt cell-cell signaling, disrupt cell-cell metabolic interactions, and/or disrupt adhesion to surfaces.

In some embodiments, L-arginine induces one or more of the above and these work individually and collectively to kill and/or reduce cell-activity and reduce biofilm biomass. In some embodiments, this also allows for improved killing with antimicrobials (e.g. L-arginine—antimicrobial agents or cocktails).

In some embodiments, the present invention provides compositions comprising L-arginine, alone or in combination with a pharmaceutically acceptable carrier or other desired delivery material (e.g., cleaner or disinfectant, etc.).

In some embodiments, the present disclosure provides compositions (e.g., dental care compositions such as toothpaste, mouthwash, etc.) comprising L-arginine in combination with e.g., CPC.

Pharmaceutical compositions and formulations for topical administration may include transdermal patches, ointments, lotions, creams, gels, drops, suppositories, sprays, liquids, mouthwash, and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Pharmaceutical compositions of the present disclosure include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations, which may conveniently be presented in unit dosage form, may be prepared according to conventional techniques well known in the pharmaceutical industry.

The compositions may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions, such as dyes, flavoring agents, preservatives, antioxidants, opacifiers, thickening agents and stabilizers. However, such materials, when added, should not unduly interfere with the biological activities of the components of the compositions. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the active agents of the formulation.

In some embodiments, the pharmaceutical composition contains a) L-arginine, and b) one or more other agents useful in killing or preventing the growth of microorganisms (e.g., antibiotics) or impacting the growth, formation or health impact or microorganisms in biofilms.

In some embodiments, the present invention provides kits, pharmaceutical compositions, or other delivery systems for use of L-arginine in treating or preventing bacterial infections or biofilms present on surfaces (e.g., dental plaque). The kit may include any and all components necessary, useful or sufficient for research or therapeutic uses including, but not limited to, L-arginine, pharmaceutical carriers, and additional components useful, necessary or sufficient for treating or preventing bacterial infections. In some embodiments, the kits provide a sub-set of the required components, wherein it is expected that the user will supply the remaining components. In some embodiments, the kits comprise two or more separate containers wherein each container houses a subset of the components to be delivered. Optionally, compositions and kits comprise other active components in order to achieve desired therapeutic effects.

In some embodiments, L-arginine is used to kill bacteria in coaggregates or biofilms. The compositions comprising L-arginine described herein find use in the killing or inhibition of growth of a variety of microorganisms (e.g., pathogenic bacteria or fungi). In some embodiments, L-arginine or compositions comprising L-arginine find use in the treatment of bacterial infections in or on the body (e.g., bacterial infections in coaggregates or biofilms). In some embodiments, L-arginine or compositions thereof are used to treat bacterial infections in wounds, sepsis, pathogenic bacterial infections in the stomach or intestine, and the like.

In some embodiments, pharmaceutical compositions are administering in a maintenance or ongoing manner (e.g., one or more times a day, two or more times a day, one or more times a week, etc.). In some embodiments, compositions are administered continuously (e.g., via a skin patch, bandage, or time release formulation). In some embodiments, compositions are administered once, twice, 5 times, 10 times or more. In some embodiments, compositions are administered over a period of weeks, months, years or indefinitely In some embodiments, L-arginine or compositions comprising L-arginine find use in the decontamination of medical devices (e.g., catheters, speculums, and the like) or implantable medical devices (e.g., pacemakers, internal defibrillators, artificial joints or bones and the like).

In some embodiments, L-arginine or compositions comprising L-arginine find use in the decontamination of surfaces (e.g., surfaces comprising biofilms). Examples include but are not limited to, household surfaces, hospital or clinical surfaces (e.g., exam tables, operating rooms, etc.), and the like.

In some embodiments, L-arginine or compositions comprising L-arginine find use in the decontamination or protection of food or food preparation areas. For example, in some embodiments, L-arginine is applied to a food after harvest to protect against future contamination or treat existing contamination.

In some embodiments, L-arginine or compositions comprising L-arginine find use in treating and/or preventing dental carries and gum disease. In some embodiments, L-arginine is added to mouthwash, toothpaste, or other oral care products.

II. Screening Compositions and Methods

Embodiments of the present disclosure provide compositions and methods for determining levels of biofilm components (e.g. arginine or AI-2) in biofilms or planktonic cells. Arginine is internalized by streptococci and sensed through the action of three different, but related, regulatory proteins: ArcR, AhrC and ArgR. These alter their conformation when they bind to arginine so that they either bind to promoter sequences or are released from promoters.

Accordingly, embodiments of the present disclosure provide a plasmid that reports expression or concentration of a component in a biofilm or planktonic cell culture. In some embodiments, the plasmid comprises a first detectable (e.g., fluorescent) marker under the control of a bacterial promoter that is constitutively expressed or a second marker (e.g., a different color fluorescent label), that is induced by the component in the biofilm (e.g., arginine or AI-2 present in the biofilm or cell culture). The present disclosure is not limited to particular promoters or reporter genes. Examples of fluorescent markers include, but are not limited to, luciferase, chloramphenicol acetyltransferase, green fluorescent protein (GFP), or Mcherry. In some embodiments, the promoter is a streptococcal promoter (e.g., a promoter active in *S. gordonii* such as, e.g., *S. gordonii* DL1 50S ribosomal protein (SGO_1192), *S. gordonii* argC or arcA promoters, or catabolite control protein A (SGO_0773)). In some embodiments, the 50S ribosomal protein promoter or other streptococcal ribosomal promoters or lactococcal promoters such as usp45 serve as control promoters for constitutive expression of the first marker. In some embodiments, catabolite control protein A promoter is a reporter of AI-2. In some embodiments, argC or arcA promoters are responsive to arginine.

In some embodiments, the present disclosure provides methods of using the plasmids described herein to monitor concentration of components (e.g., arginine or AI-2) of a biofilm or planktonic cell population (e.g., in a streptococcal spp. such as *S. gordonii*), comprising: a) contacting a streptococcal cell with the promoters described herein; and b) measuring the level of marker. In some embodiments, the level of signal from the marker under the control of the promoter induced by the external biofilm component or the constitutive promoter is compared to level of signal from known quantities/concentrations of the component (e.g., a standard curve). In some embodiments, the level of fluorescence is then be correlated in a fluorimeter or imaging system.

In some embodiments, the reporter plasmids and methods find use in research, screening (e.g., drug screening), and diagnostic applications. For example, in some embodiments, test compounds (e.g., antimicrobial drugs) are added to a biofilm or planktonic cell population and the effect of the test compound on levels of biofilm components (e.g., arginine) is assayed.

EXPERIMENTAL

The following examples are provided in order to demonstrate and further illustrate certain preferred embodiments and aspects of the present invention and are not to be construed as limiting the scope thereof.

Example 1

Figure 2:
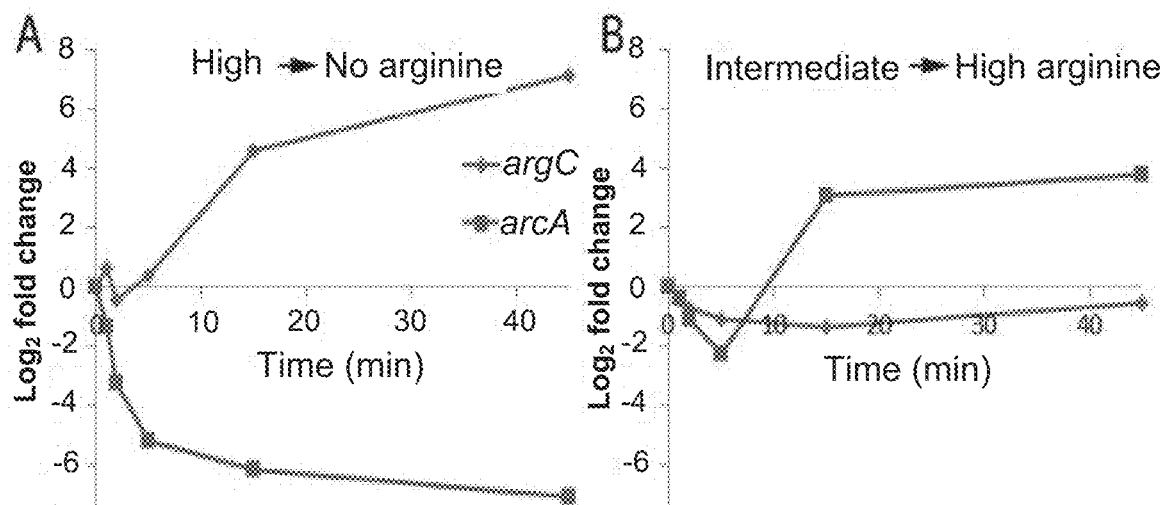
FIG. 2 shows regulation of S. gordonii argC and arcA gene expression in response to rapid changes in exogenous L-arginine. (A) S. gordonii cells were cultured in high (5 mM) arginine and switched to no arginine at time=0 min on x-axis. (B) S. gordonii was cultured in intermediate (0.5 mM) arginine to late exponential phase, when excess (50 mM) arginine was added (time=0 min).

This example relates to biofilms formed by single species of bacteria. In these systems, L-arginine has diverse effects on bacterial gene regulation, phenotype, metabolism and biofilm formation.
Arginine Sensing Triggers Gene Regulation.
*S. gordonii* contains the full genetic pathway for biosynthesis of L-arginine. However, like *S. aureus*, it is a functional arginine auxotroph under laboratory conditions (Jakubovics et al., supra, Nuxoll et al., PLoS pathogens. 2012; 8(11):e1003033). A shift from arginine-replete medium to arginine-deficient medium resulted in a marked change in phenotype of *S. gordonii*. In addition to genes previously shown to be regulated by coaggregation, there was a significant decrease in the expression of several well-characterized cell surface adhesins (Table 1). In general, metabolism was decreased with the exception of the arginine biosynthesis pathway, which was strongly up-regulated (FIG. 2). These data are consistent with the development of a specialized biofilm dispersal cell state, similar to that produced by the dimorphic aquatic bacterium *Caulobacter crescentus*, upon nutrient limitation (England et al., Journal of bacteriology. 2010; 192(3):819-33.). This example relates to biofilms formed by single species of bacteria. In these systems, L-arginine has diverse effects on bacterial gene regulation, phenotype, metabolism and biofilm formation.
Biofilm Formation in an Environmentally Germane Microfluidic Biofilm System.

Figure 3:
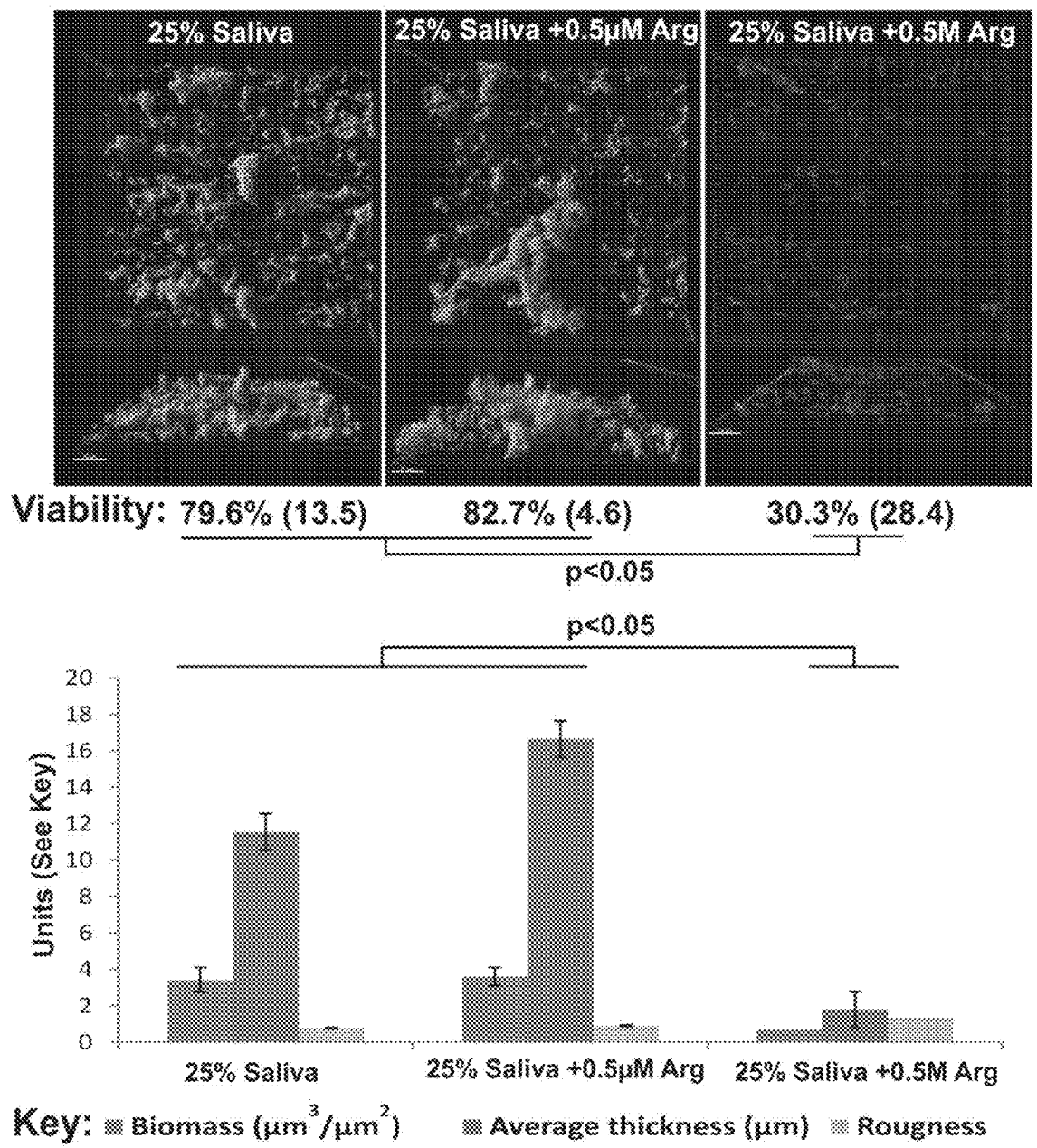
FIG. 3 shows S. gordonii biofilms in saliva with or without 0.5 mM or 0.5 M (500 mM) arginine (Arg).

The effects of arginine-dependent dosing of *S. gordonii* biofilms is assessed in a modified Bioflux microfluidics system. Human saliva is collected and pooled from ≥6 different volunteers (Cuadra-Saenz et al., Microbiology. 2012; 158(Pt 7):1783-95), diluted to 25%, and additional supplements (e.g. sucrose, haemin, BHI) added as required to simulate different conditions. Note, we grow robust biofilms in even non-supplemented saliva and pooling the saliva minimizes variation in salivary components. To obtain an indication of free arginine levels in pooled saliva, arginine is measured in ≥3 different pooled saliva samples using standard techniques (Jakubovics et al., supra; Van Wuyckhuyse et al., Journal of dental research. 1995; 74(2):686-90). The 24 channels of the Bioflux system are coated with saliva, inoculated with monocultures of *S. gordonii* (or multi-species biofilms harvested form saliva) and biofilms are developed at 37° C. with cell free saliva. After 20 h, cells are stained with live/dead stain and visualized using a Leica SPE CLSM. Biomass and structural biofilm parameters are quantified using COMSTAT (Heydorn et al., Microbiology. 2000; 146 (Pt 10):2395-407), ImageJ (Collins, Biotechniques. 2007; 43(1 Suppl):25-30), and IMARIS software (Bitplane, Switzerland). FIG. 3 shows that high concentrations of arginine (500 mM) significantly reduce the extent of biofilm present.
Arginine and Bacterial Biofilm Formation.

Arginine has been shown to play a key role in biofilm formation and host colonization by Gram-positive and Gram-negative bacteria. For example, at physiological concentrations found in cystic fibrosis sputum, arginine promotes *P. aeruginosa* biofilm formation (Bernier et al., Research in microbiology. 2011; 162(7):680-8). Arginine was the only amino acid that prevented swarming by *P. aeruginosa*, and thus plays a pivotal role in promoting a sessile lifestyle in this species (Bernier et al., supra). In *S. aureus*, the final gene in the arginine biosynthesis pathway, argH, is essential for virulence in a mouse kidney abscess model, indicating that arginine is restricted in vivo (Nuxoll et al., supra). Many oral streptococci are auxotrophic or conditionally auxotrophic for arginine (Jakubovics et al., supra, Cowman et al. Applied microbiology. 1975; 30(3): 374-80; Terleckyj et al., Infect Immun. 1975; 11(4):656-64; Cowman et al., Applied microbiology. 1974; 27(1):86-92; Rogers et al., Journal of general microbiology. 1990; 136 (12):2545-50). The importance of the *S. gordonii* arginine biosynthesis pathway for growth in salivary biofilms is investigated using an argH mutant and a complemented strain. The present invention is not limited to a particular mechanism. Indeed, an understanding of the mechanism is not necessary to practice the present invention. Nonetheless, it is contemplated that arginine is a limiting nutrient for L-arginine biosynthesis-deficient streptococci growing as single-species colonies in salivary biofilms. Further, it is contemplated that coaggregation with other species in the biofilm overcomes the effects of L-arginine restriction but is subject to disruption by adding elevated amounts of L-arginine.

Arginine Catabolism in Biofilms.

In biofilm cells of *P. aeruginosa*, arginine metabolism is up-regulated compared with planktonic cells, due to an increase in expression of genes encoding the arginine deiminase system (ADS) (Xu et al., PloS one. 2013; 8(2):e57050; Sauer et al., Journal of bacteriology. 2002; 184(4):1140-54). The ADS is a key component of anaerobic metabolism in this organism. The switch to ADS-mediated anaerobic fermentation is linked to increased susceptibility of *P. aeruginosa* to ciprofloxacin and tobramycin (Borriello et al., Antimicrobial agents and chemotherapy. 2004; 48(7):2659-64). The ADS is also important in the pathogenicity of *S. aureus*. Indeed, the USA300 pathogenic lineage of *S. aureus* has acquired a genetic element termed the Arginine Catabolic Mobile Element (ACME), which contains genes encoding an ADS pathway and is thought to be a key factor in promoting growth and survival on the skin (Otto et al., International journal of medical microbiology: IJMM. 2013). As such, the ACME may be important for the high transmissibility of USA300 strains.

Figure 4:
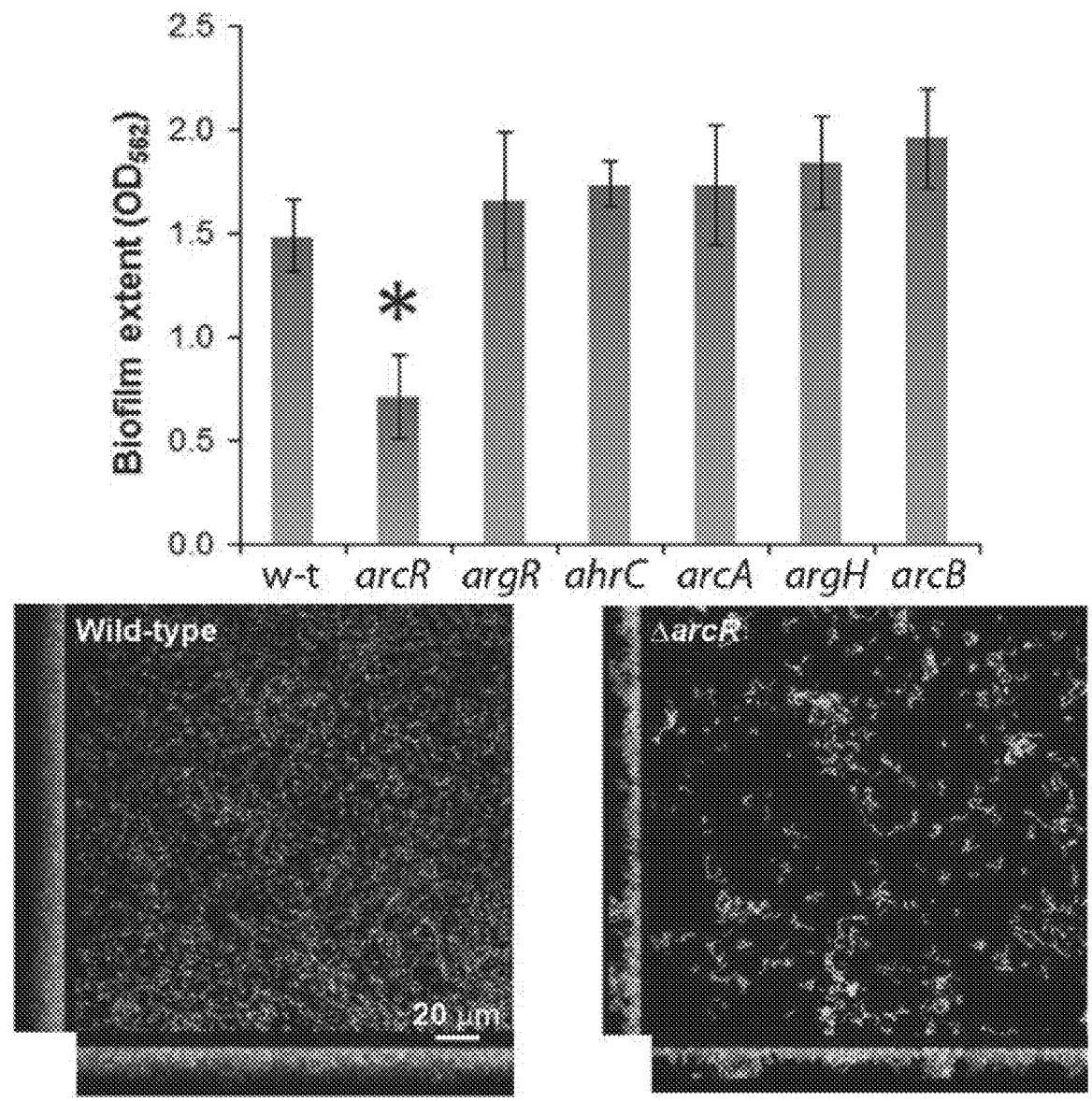
FIG. 4 shows disruption of arcR reduces biofilm formation by S. gordonii.

High concentrations of arginine negatively affect the ability of certain oral bacteria to colonize oral biofilms. Arginine has been shown to inhibit several different coaggregation interactions between oral bacteria (Edwards et al., Oral microbiology and immunology. 2007; 22(4):217-24; George et al., Oral microbiology and immunology. 1992; 7(5):285-90. PubMed PMID: 1494452; Kaplan et al., Molecular microbiology. 2009; 71(1):35-47; Takemoto et al., Journal of periodontal research. 1993; 28(1):21-6.; Nagata et al., Journal of dental research. 1990; 69(8):1476-9.). Data described herein shows that the disruption of coaggregation within oral biofilms leads to the release of bacteria from the biofilm. Nutrients induce dispersion of *P. aeruginosa* biofilms and this phenomenon involves genes required for arginine metabolism (Sauer et al., Journal of bacteriology. 2004 186(21): 7312-7326). FIG. 4 shows that in *S. gordonii* the gene encoding ArcR, the regulator of arginine deiminase system genes, is required for biofilm formation by *S. gordonii* since a strain lacking the arcR gene does not form strong biofilms. Therefore L-arginine is a central regulator of biofilm formation.

TABLE 1

Selected *S. gordonii* genes that were strongly regulated following a shift to low arginine. For multi-gene loci, the average fold change across the locus is indicated.

| Locus | Description | Fold Change |
|---|---|---|
| Upregulated (low vs high arginine) | | |
| SGO_1566-1569 | ArgDBJC, arginine biosynthesis | 339.6 |
| Downregulated (low vs high arginine) | | |
| SGO_1575-1582 | Bfb locus, biofilm formation and cellobiose PTS | −30.2 |
| SGO_2098 | RpsD, ribosomal protein 54 | −12.5 |
| SGO_1686-1700 | Fab/acc locus, fatty acid biosynthesis | −11.4 |
| SGO_2015-2028 | Receptor polysaccharide biosynthesis | −8.6 |
| SGO_0966-0978 | Hsa, secondary secretion and glycosylation systems | −4.9 |
| SGO_1591-593 | ArcABC arginine catabolism | −3.5 |

Example 2

This example describes the impact of L-arginine on oral biofilms that contain species grown under conditions representative of the human oral cavity. Using a microfluidic-based approach, using human saliva as the inoculum and 25% filter-sterilized human saliva as the nutrient source, it was demonstrated that HCL-balanced L-arginine (LAHCL) destabilizes oral biofilms in a concentration dependent manner. Destabilization was expressed as loss of biofilm structure and change in bacterial community membership, as determined by confocal laser scanning microscopy and 454 pyrosequencing. Very limited antimicrobial effects were evident and only detected as a consequence of biofilm perturbation, and the optimal concentration for destabilization was between 50 and 500 mM. No substantial changes in pH were recorded, due to the use of HCl balanced L-arginine (L-arginine monohydrochloride) and the buffering capacity of human saliva.

As traditional approaches to control oral biofilms rely heavily on antimicrobials and L-arginine was demonstrated a destabilizing effect, synergy with other antimicrobials to more effectively inactivate biofilm cells was investigated. Mixing L-arginine with cetylpyridinium chloride (CPC) resulted in at least five times greater biofilm inactivation (by live/dead staining). Taken collectively, it was demonstrated that L-arginine has broad oral biofilm destabilizing effects under conditions representative of the human mouth. Such effects are used to remove biofilms or enhance traditional CPC-based antimicrobial treatment strategies.

Figure 5:
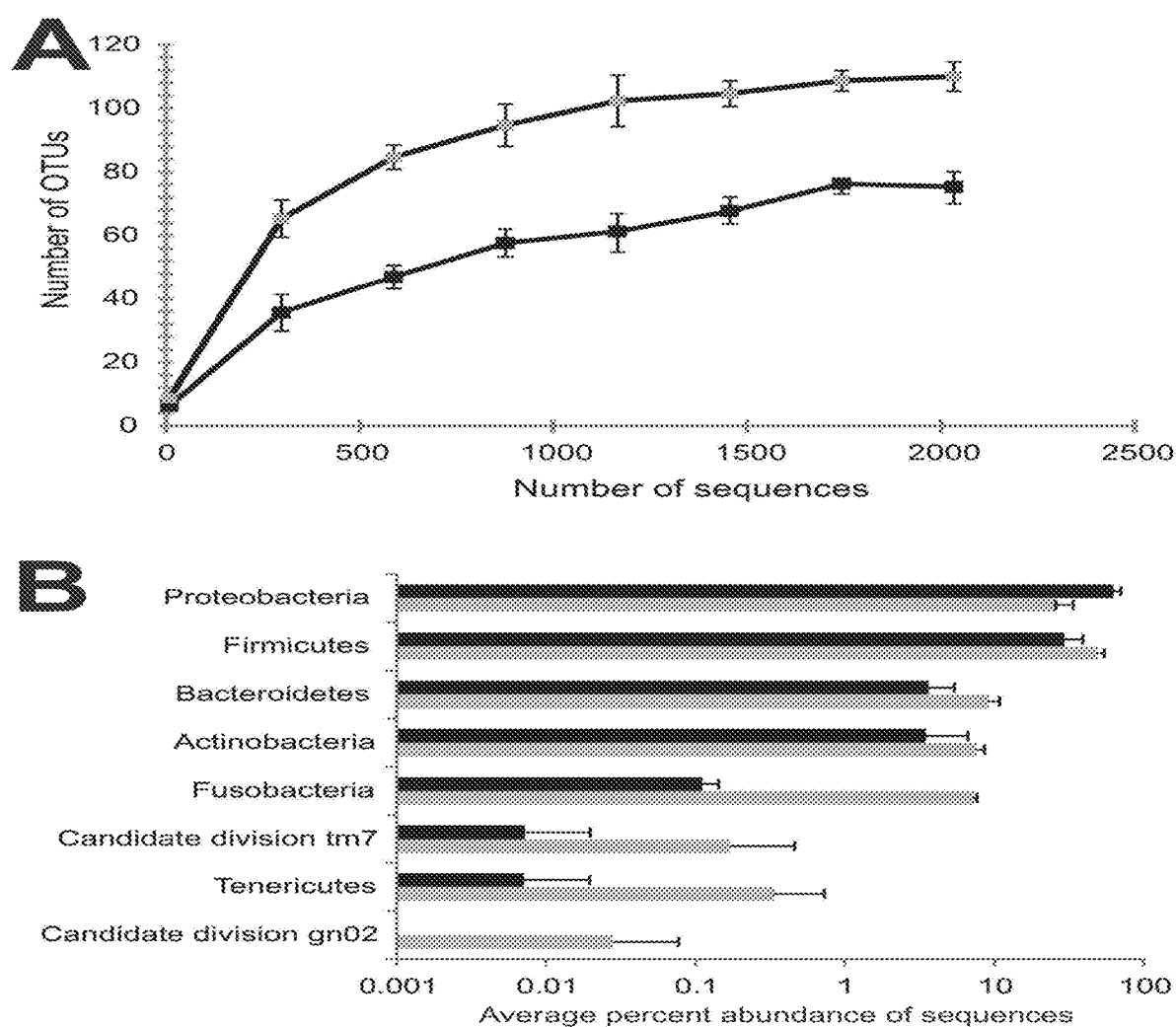
FIG. 5 shows the effect of L-arginine on species composition of saliva derived community developed in pooled filter sterilized saliva. (A) Showing the increase in bacterial diversity (operational taxonomic units, OTU) caused by prolonged exposure of oral multi-species biofilms to 500 mM L-arginine. Black-colored bars represent data derived from the analysis of biofilms developed in flowing non-supplemented saliva while the grey-colored bars represent data derived from the analysis of biofilms developed in 500 mM supplemented saliva. (B) Showing changes in phyla (color coding as before). (C) Showing changes in composition of genera (key is from left to right in order from bottom to top in bar; Neisseria, Granulicatella, Streptococcus, etc).
Figure 5:
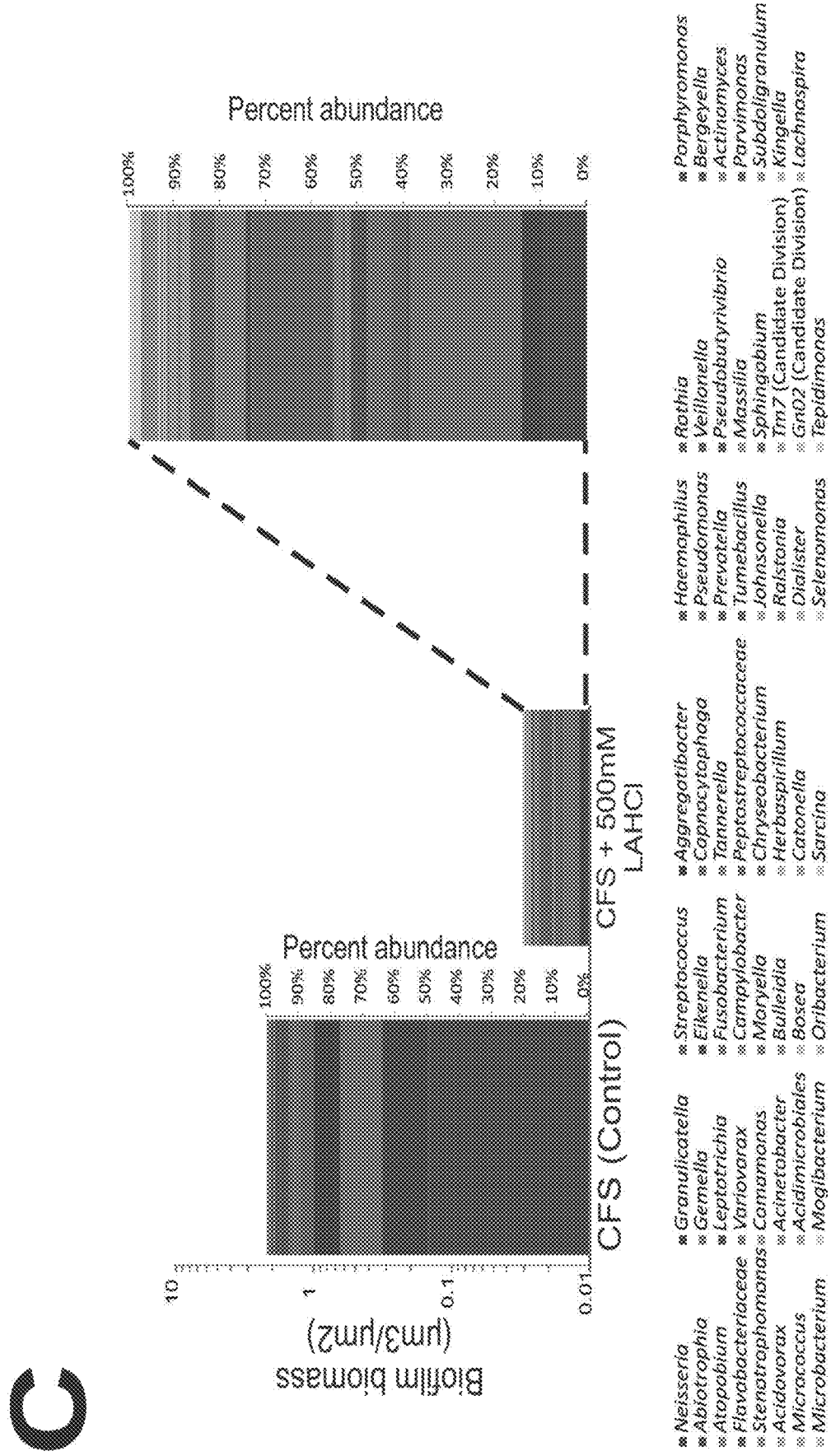
Figure 6:
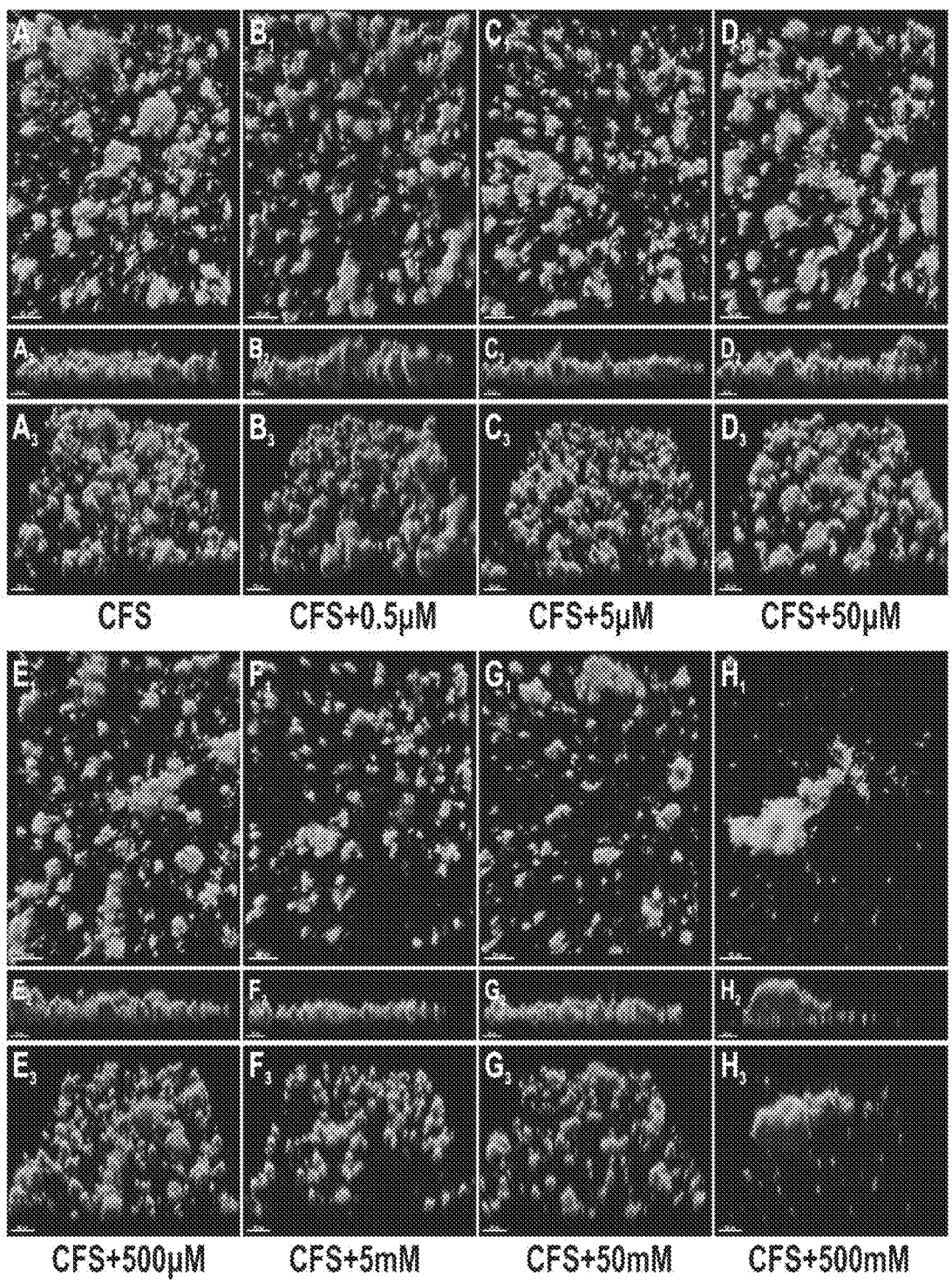
FIG. 6 shows the effect of growing multi-species biofilms in increasing concentrations of L-arginine under static conditions. Representative 3D renderings of 20 h-old oral biofilms grown from a cell-containing saliva (CCS) inoculum in the static biofilm system containing cell free saliva (CFS) supplemented with different concentrations of L-arginine monohydrochloride (LAHCl). Upper renderings ($A_1$-$H_1$) are of the x-y plane. Middle renderings ($A_2$-$H_2$) are of the x-z plane. Lower renderings ($A_3$-$H_3$) represent an angled view (x-y-z). Bars represent 50 µm. Associated table shows changes in mean percentage cell viability.

Results are shown in FIGS. 5-11. FIG. 5 shows changes in community composition of L-arginine (500 mM) treated biofilms. FIG. 6 shows the effect of L-arginine (CLSM) on multi-species biofilms of bacteria in saliva derived community developed in pooled filter sterilized saliva in a static (non-flowing) microplate system. 500 mM L-arginine destabilized multi-species oral biofilm communities to reduce biofilm biomass (and therefore total numbers of bacteria, including pathogens) and also makes the biofilm more diffuse with respect to architecture. No substantial killing was observed although there is a slight statistically significant increase in red "signal" indicating that the non-responsive dead/damaged cells are left behind in the biofilm.

Figure 7:
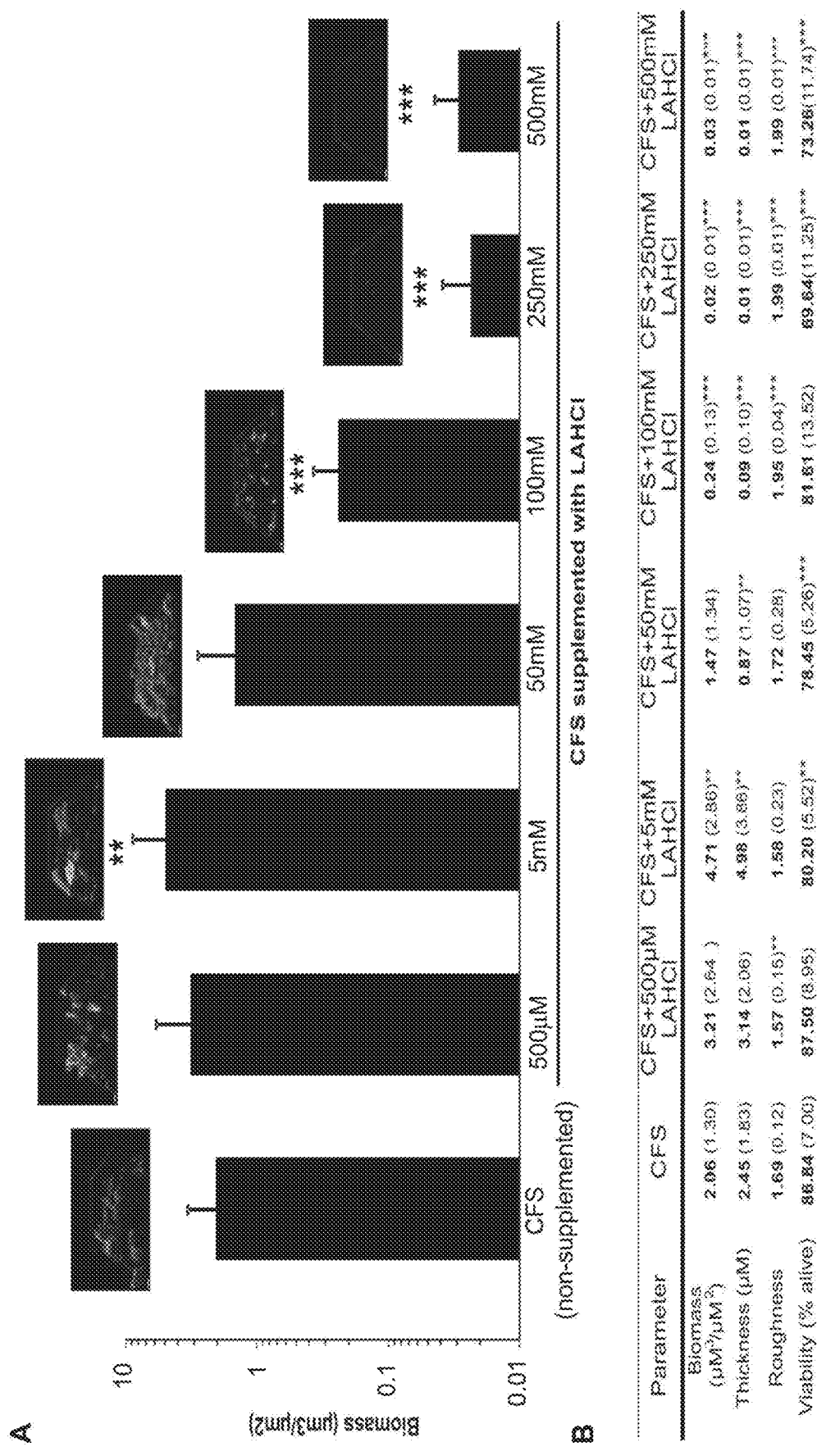
FIG. 7 shows that L-arginine destabilizes the architecture of multi-species oral biofilms grown in saliva under flowing conditions in a microfluidics channel. Representative 3D renderings and biofilm characteristics derived from computational image analysis of oral biofilms developed for 20 h in different concentrations of L-arginine monohydrochloride (LAHCl) in the Bioflux™ flowing saliva biofilm system.

FIG. 7 shows Representative 3D renderings and biofilm characteristics derived from computational image analysis of oral biofilms developed for 20 h in different concentrations of L-arginine monohydrochloride (LAHCl) in the Bioflux™ flowing saliva biofilm system. Green signal indicates viable live cells and red signal indicates damaged/dead cells. Associated table shows changes in cell viability, biofilm biomass, thickness, and roughness. Data derived from at-least 18 renderings across three experiments and standard deviations are shown in brackets. *P<0.05; P<0.01; P<0.001: significant differences from the CFS control.

Figure 8:
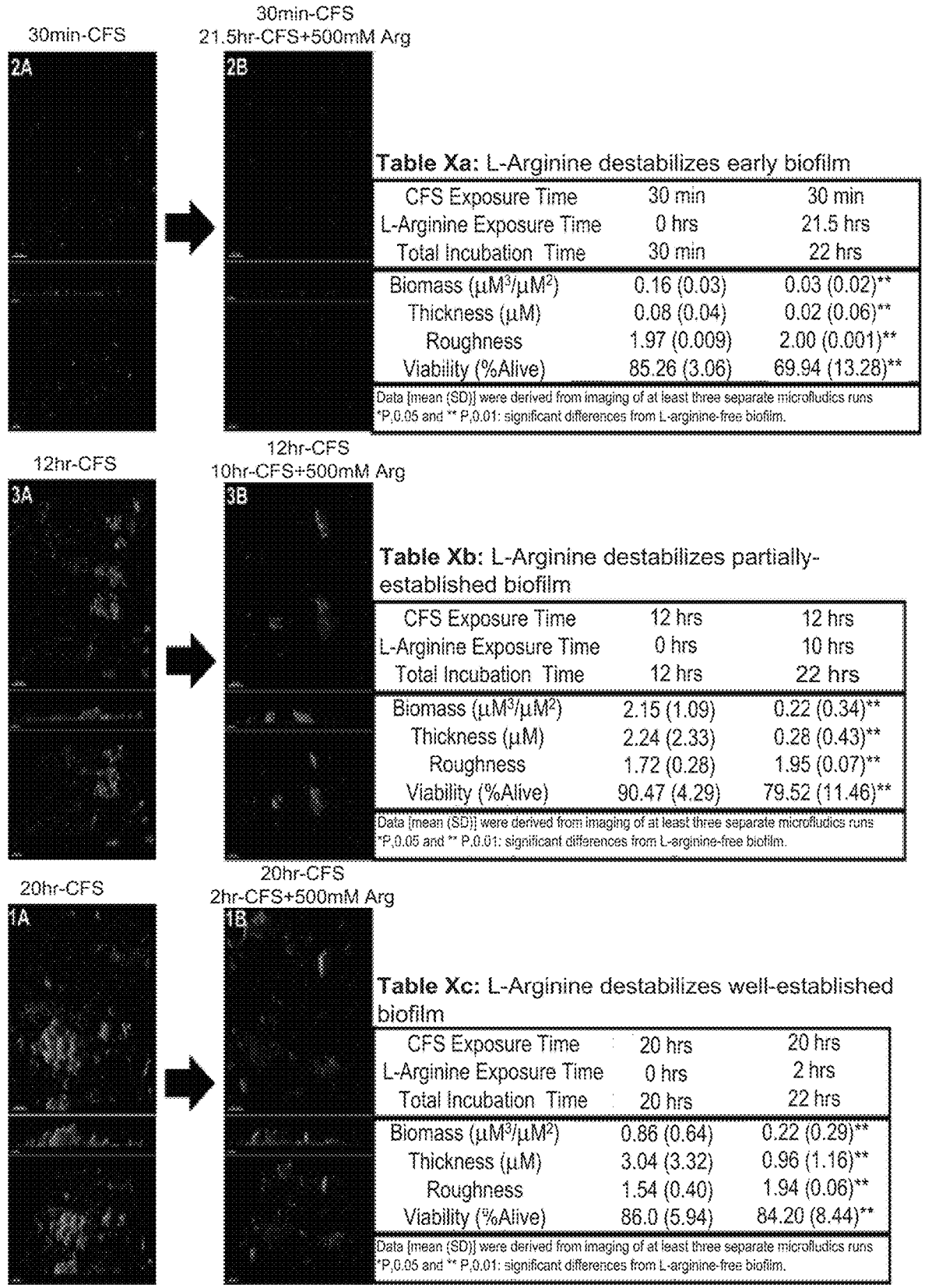
FIG. 8 shows that 500 mM L-arginine destabilizes preformed multi-species oral biofilms of differing developmental age.

FIG. 8 shows that 500 mM L-arginine destabilizes preformed multi-species oral biofilms of differing developmental age.

Figure 9:
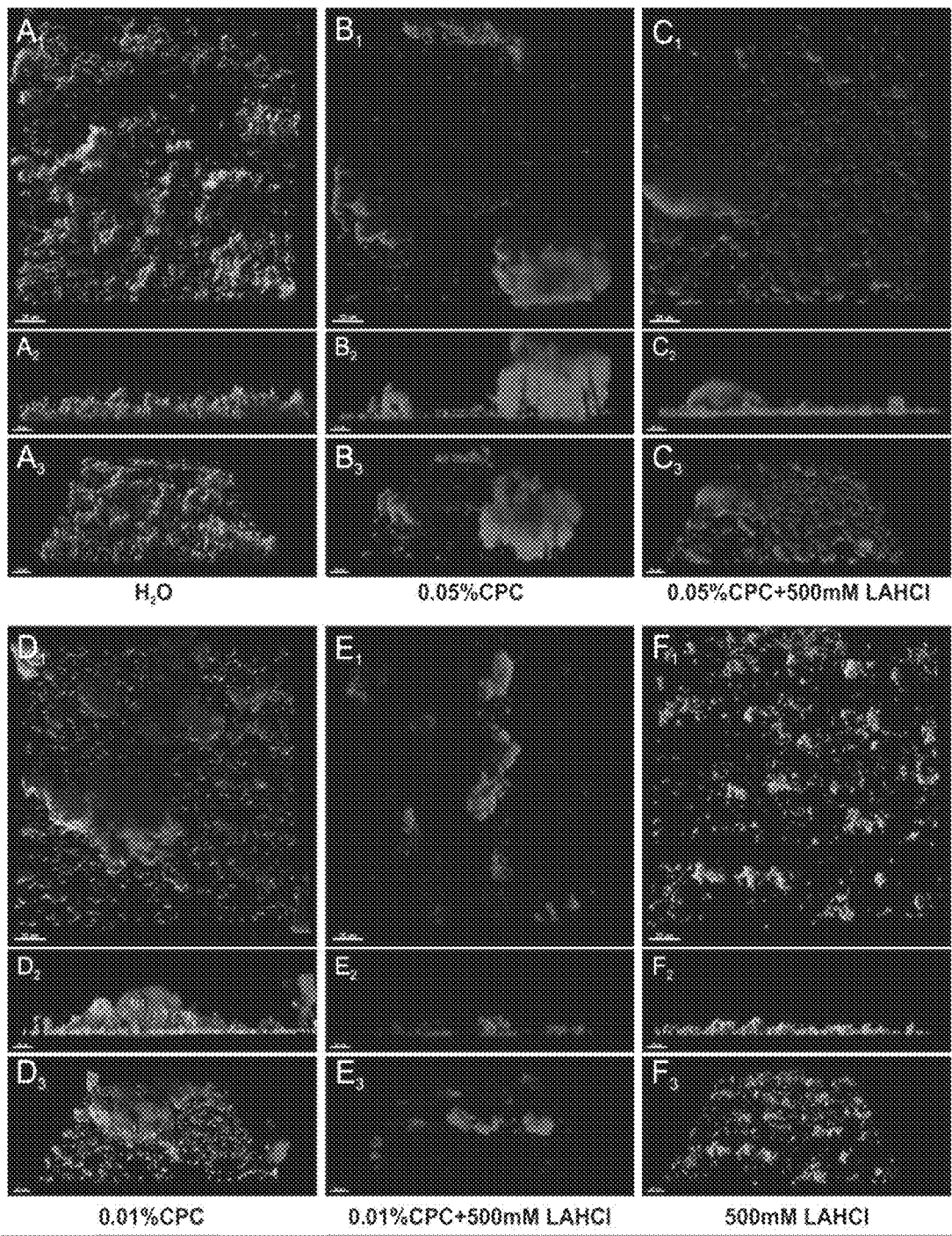
FIG. 9 shows that L-arginine destabilizes pre-formed multi-species oral biofilm communities and in doing so can enhance the penetration of CPC (0.01 or 0.05%). Specifically, this figure shows that 500 mM L-arginine enhances the penetration and killing of CPC so that less CPC is required as compared to when used in the absence of L-arginine.

FIG. 9 shows that L-arginine destabilizes multi-species oral biofilm communities to enhance the penetration of CPC. As a consequence, lower CPC concentrations are used to achieve the same level of killing/inactivation/cell damage.

Figure 10:
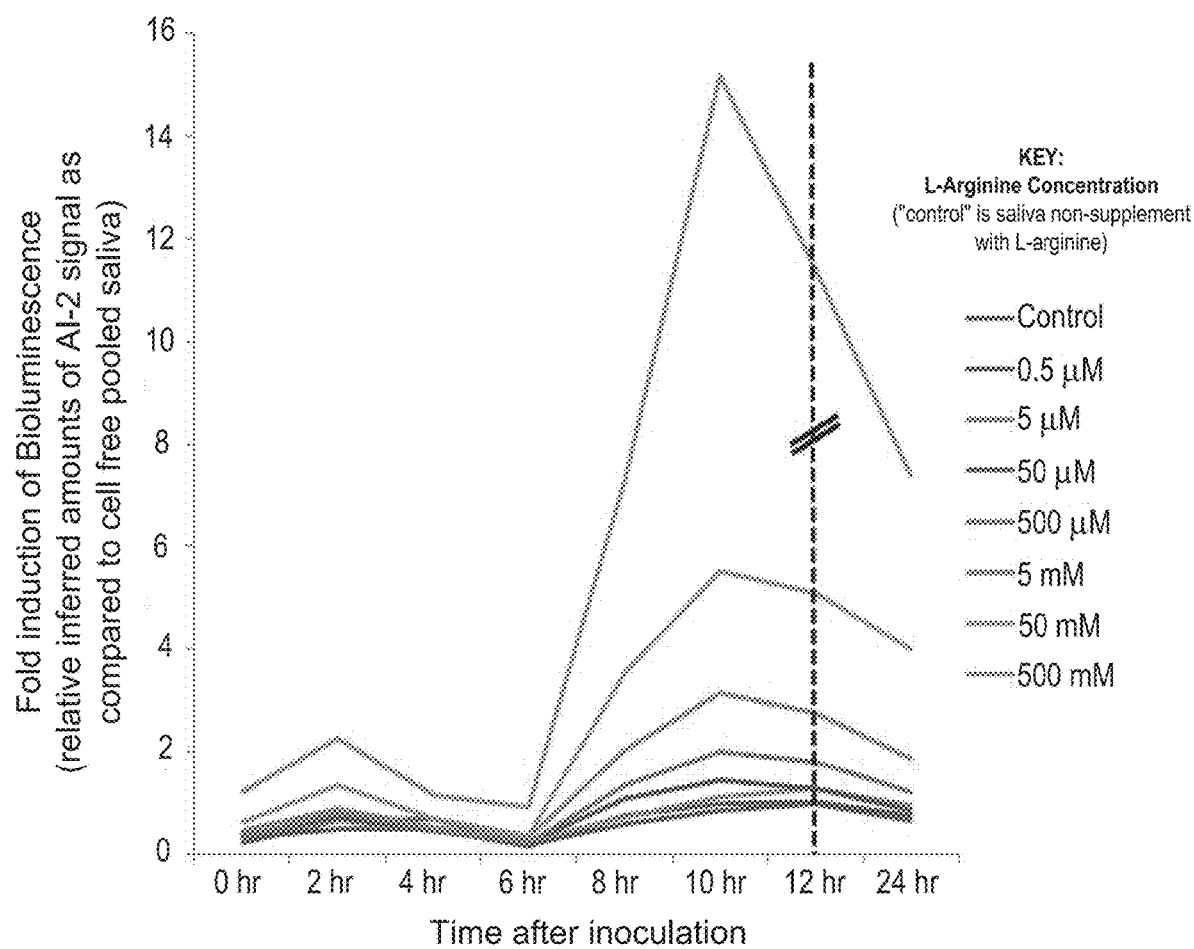
FIG. 10 shows fold induction of bioluminescence by Vibrio harveyi BB170 which is responsive to AI-2. AI-2 is shown to be produced in increasing amounts as L-arginine concentration increases. The AI-2 data are normalized to the "control" (non-supplemented saliva).

FIG. 10 shows fold induction of luciferase production in the *Vibrio harveyi* reporter strain BB170 normalized to a positive control (BB152). A control run of plain CFS (cell-free saliva) with the given concentrations of arginine was compared to microfluidics efflux, which contains any secreted molecules from bacteria grown with the given concentration of L-arginine. Values were produced by first taking averages of 4 trials at each concentration and dividing them by the average for the negative control, creating an induction number. The amount of AI-2 produced from multi-species biofilms increases as the concentrations of arginine used to treat them increases. This indicates that L-arginine energizes bacterial communities, because AI-2 is a proxy for metabolism. High AI-2 may also have a destabilizing effect on the community, which could explain or contribute to the structural changes seen in the biofilms.

Figure 11:
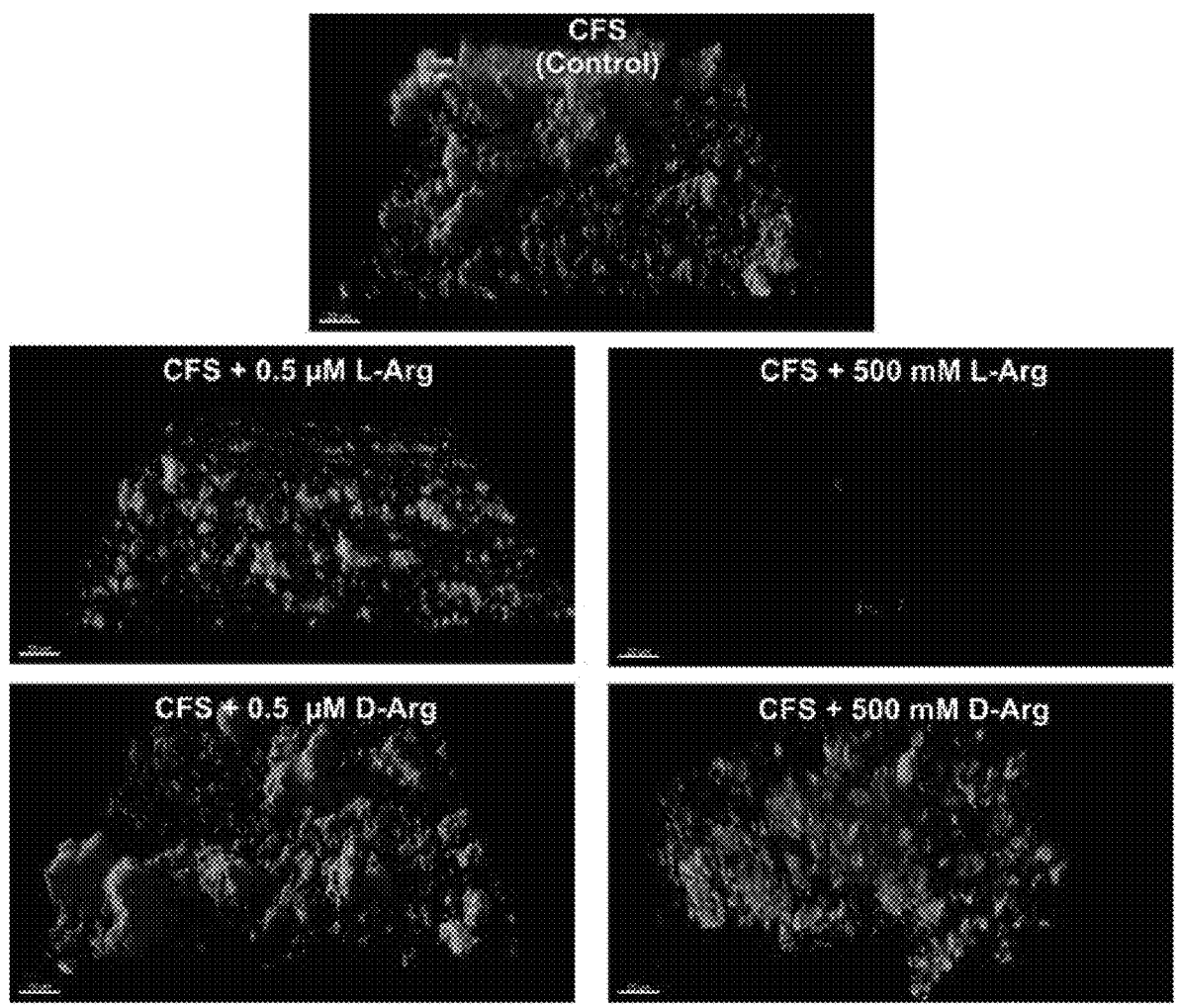
FIG. 11 shows that application of L-arginine but not D-arginine destabizes and prevents growth of bacterial communities.

FIG. 11 shows that application of L-arginine disrupts bacterial biofilm communities but D-arginine does not have the same effect. Therefore the destabilizing effects of arginine are specific to the L-form.

In conclusion, these examples demonstrate that L-arginine reduces the pathogenic potential of biofilms by reducing the biofilm biomass and reducing the total amount and proportion of pathogens; L-arginine augments/enhances the activity of antimicrobials such as CPC. This is through enhancing access of antimicrobial by loosening biofilm and also by altering the growth-rate of the bacteria; L-arginine causes cell-cell signaling dysregulation; L-arginine is a combinational treatment that up-regulates metabolism, alters cell-cell signaling, and inhibits cell-cell adhesion; and L-arginine increases the proportion of beneficial bacteria that can combat the negative effects of pathogens such as *S. mutans*. The proportion of *Veillonella* species are increased in biofilms as are the proportions of non-cariogenic streptococci.

Example 3

Figure 12:
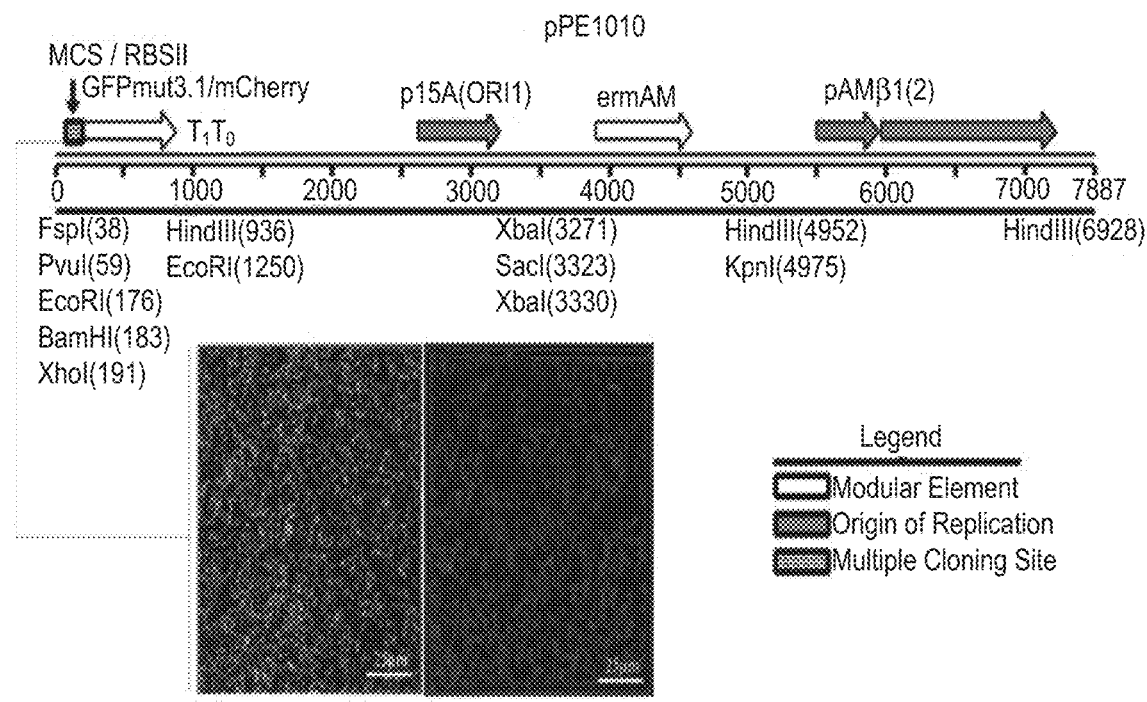
FIG. 12 shows (A) modifiable plasmid (pPE1010) to allow the generation of fluorescent Streptococcus gordonii DL1 (GFP or Mcherry) and (B) an example of two promoter that allow the evaluation of the differential expression of GFP fluorescence in S. gordonii DL1 biofilms in response to exogenously added AI-2.
Figure 12:
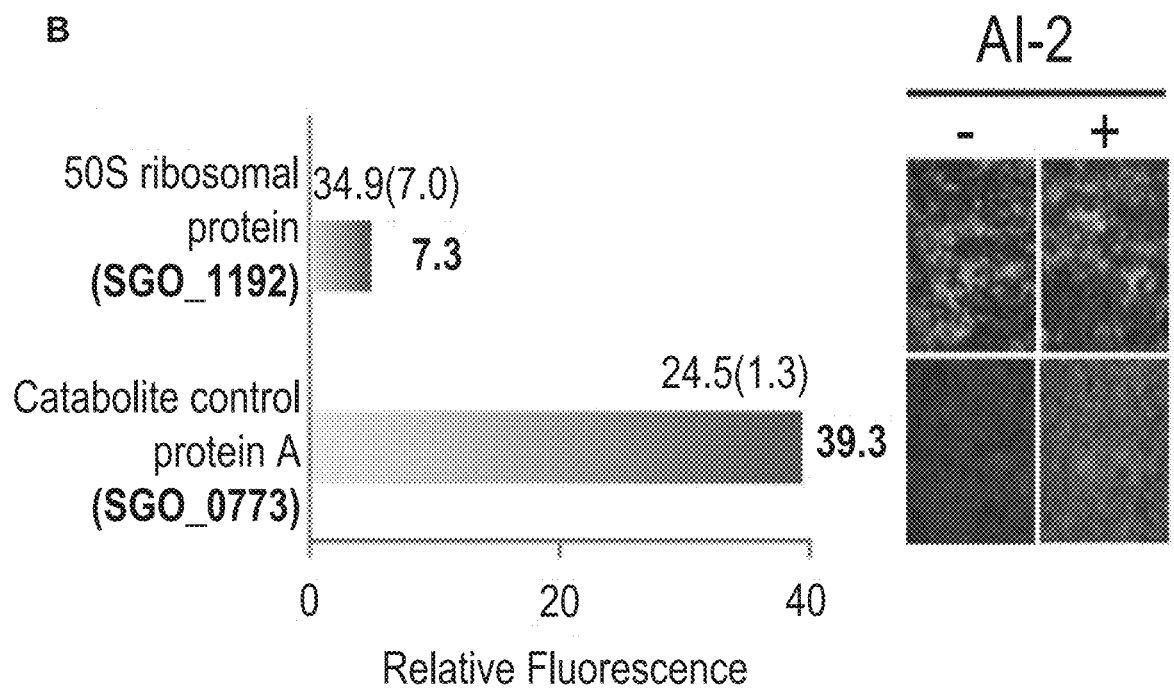

A plasmid (See e.g., FIG. 12) was utilized to monitor expression of reporter genes in the presence of arginine or AI-2. The pPE1010 backbone described in England et al. (Proc Natl Acad Sci USA. 2004 Nov. 30; 101(48):16917-22. Epub 2004 Nov. 16) was modified to express fluorescent genes such as GFP or Mcherry in *S. gordonii* DL1 or other species of streptococci. Specifically, promoters from differentially regulated genes are inserted upstream of a GFP or Mcherry gene harbored on pPE1010 (or similar streptococcal plasmid shuttle vector system) to be differentially expressed (FIGS. 12A and 12B). An example was performed (FIG. 12B) showing minimal differential expression by a 50S ribosomal protein (SGO_1192; gene rplJ responsible for the highly abundant 50S ribosomal protein L10) when exposed to exogenously added autoinducer-2 (AI-2) as compared to drastically different gene expression by the catabolite control protein A (SGO_0773; ccpA). The plasmid provides constitutive-producing fluorescent probes for monitoring bacteria in biofilms and reporter systems that report arginine (or AI-2) concentrations in biofilms such as those found in dental plaque biofilms.

All publications, patents, patent applications and accession numbers mentioned in the above specification are herein incorporated by reference in their entirety. Although the invention has been described in connection with specific embodiments, it should be understood that the invention as claimed should not be unduly limited to such specific embodiments. Indeed, various modifications and variations of the described compositions and methods of the invention will be apparent to those of ordinary skill in the art and are intended to be within the scope of the following claims.

The invention claimed is:

1. A plasmid that reports concentration of arginine in a biofilm or planktonic cell population, wherein said plasmid comprises a fluorescent marker under the control of a promoter induced by arginine, wherein said promoter induced by arginine is selected from the group consisting of *S. gordonii* catabolite control protein A (SGO_0773) promoter, *S. gordonii* argC promoter, and *S. gordonii* arcA promoter.

2. The plasmid of claim 1, wherein said fluorescent marker is green fluorescent protein (GFP) or Mcherry.

3. A streptococcal cell comprising the plasmid of claim 1.

4. The streptococcal cell of claim 3, wherein said cell is *S. gordonii*.

5. The streptococcal cell of claim 3, wherein said cell is present in a biofilm.

6. A method of monitoring the concentration of arginine in a biofilm comprising:
   a) contacting the streptococcal cell of claim 3 comprising the promoter; and
   b) measuring the level of expression of said fluorescent marker, wherein the level of expression of said fluorescent marker is correlated to the concentration of said arginine.

7. The method of claim 6, further comprising the step of contacting said streptococcal cell with a test compound.

8. The method of claim 7, wherein said test compound is an antimicrobial drug.

* * * * *